United States Patent [19]
Robins

[11] Patent Number: 5,235,186
[45] Date of Patent: Aug. 10, 1993

[54] PROBE-BASED ELECTROSPRAY ADAPTER FOR THERMOSPRAY EQUIPPED QUADRUPOLE BASED LC/MS SYSTEMS

[75] Inventor: Russell H. Robins, Kalamazoo, Mich.

[73] Assignee: Finnigan Mat, Inc., San Jose, Calif.

[21] Appl. No.: 826,922

[22] Filed: Jan. 24, 1992

[51] Int. Cl.⁵ .................. B01D 59/44; H01J 49/00
[52] U.S. Cl. ........................... 250/288; 250/281
[58] Field of Search ................. 250/281, 282, 288

[56] References Cited

U.S. PATENT DOCUMENTS

| | | | |
|---|---|---|---|
| 4,298,795 | 11/1981 | Takeuchi et al. | 250/288 |
| 4,531,056 | 7/1985 | Labowsky et al. | 250/288 |
| 4,885,076 | 12/1989 | Smith et al. | 204/180.1 |
| 4,977,320 | 12/1990 | Chowdhury et al. | 250/281 |
| 5,015,845 | 5/1991 | Allen et al. | 250/282 |
| 5,073,713 | 12/1991 | Smith et al. | 250/282 |
| 5,122,670 | 6/1992 | MyLchreest et al. | 250/282 |

*Primary Examiner*—Bruce C. Anderson
*Attorney, Agent, or Firm*—Flynn, Thiel, Boutell & Tanis

[57] ABSTRACT

A probe adapter for converting a thermospray equipped LC/MS analyzer to an electrospray equipped LC/MS analyzer. The probe adapter includes structure defining an elongated and hollow first chamber opened at one end to atmosphere and closed at the other end by a first partition. Additional structure is provided defining a hole through the first partition and an elongated and hollow probe shaft is connected to and extends from the first partition on a side thereof remote from the opened end. A central axis of the probe shaft is coaxial with a central axis of the first hole. A second partition is provided in the first chamber and is spaced from the first partition and defines a second chamber therebetween. Adjusting structure is provided for selectively adjusting the spacing between the two partitions. A second hole is provided in the second partition and is coaxially aligned with the first hole. An elongated and hollow drift tube is mounted inside the probe shaft, an inlet end of the drift tube extending through the first hole in the first partition and terminating in the second chamber. An outlet end of the drift tube extends a finite distance beyond an end of the probe shaft remote from the first partition. The relative spacing between the first and second partitions determines a spacing between the inlet end of the drift tube and the second hole.

8 Claims, 14 Drawing Sheets

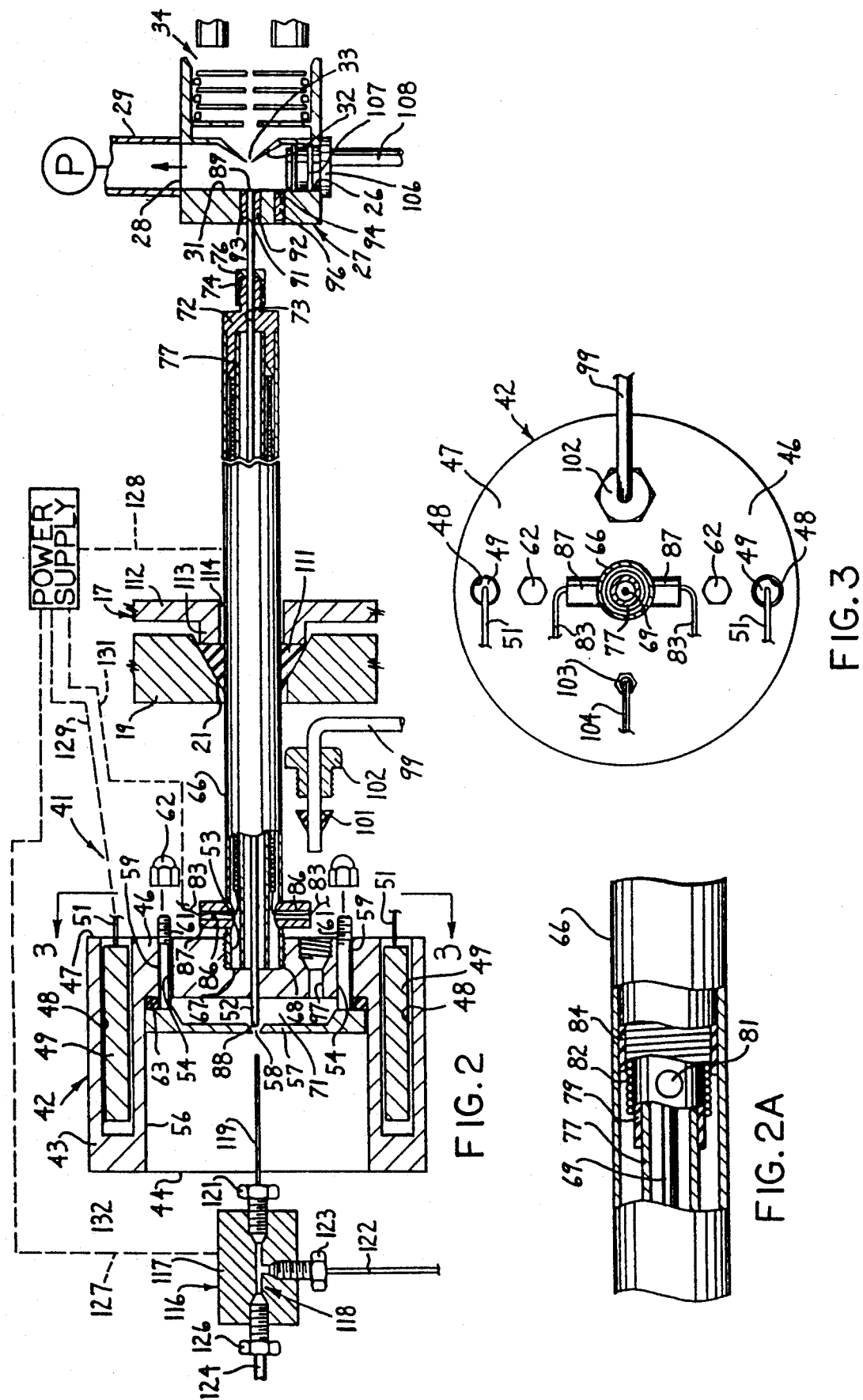

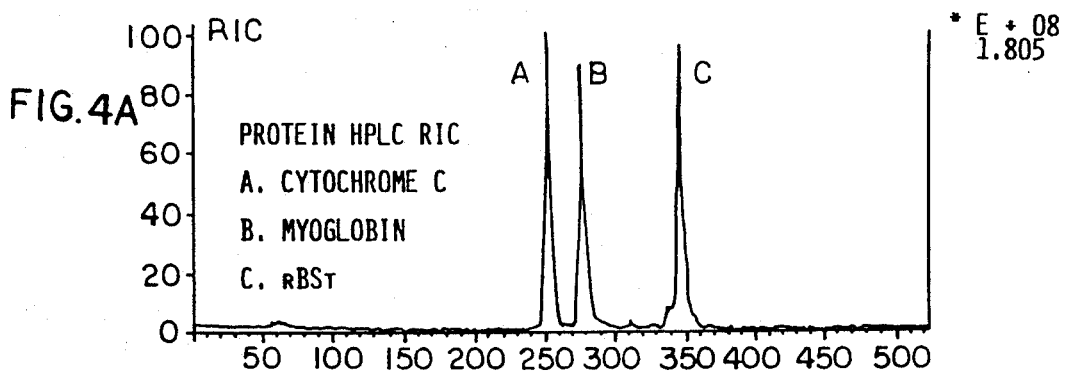
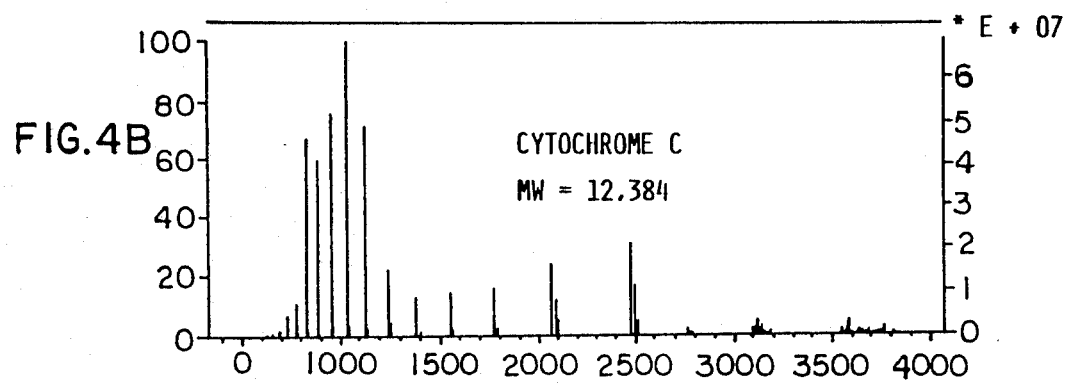
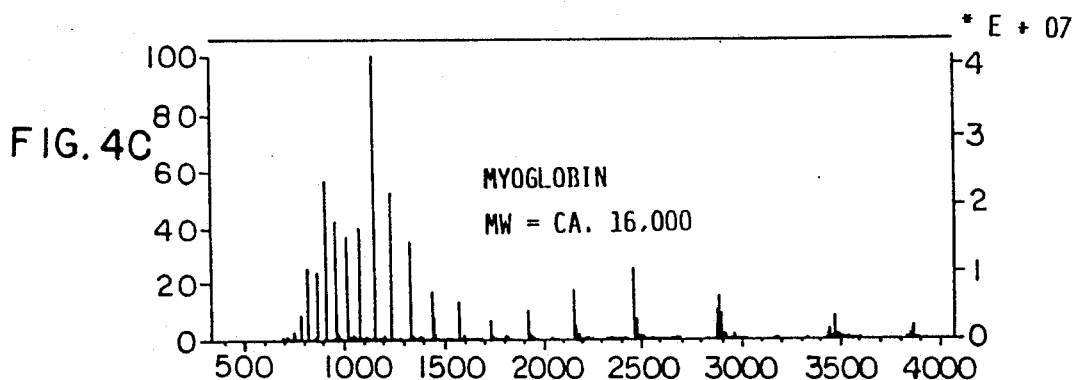
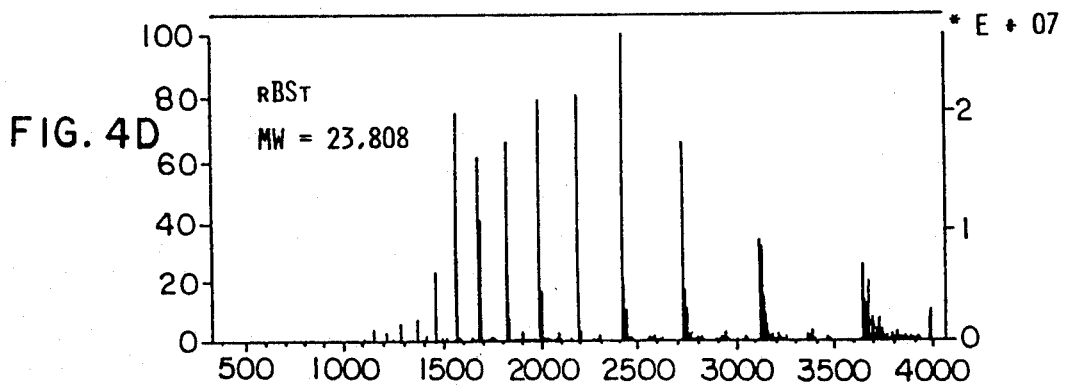
ON-LINE ESI/LC/MS ANALYSIS OF CYTOCHROME C, MYOGLOBIN, AND ROCOMBINANT BOVINE SOMATOTROPIN (RBST).

ESI/MS SPECTRUM OF CD4-PE40 (MW=60kDa) SHOWING CHARGE STATES IN EXCESS OF +50 CHARGES.

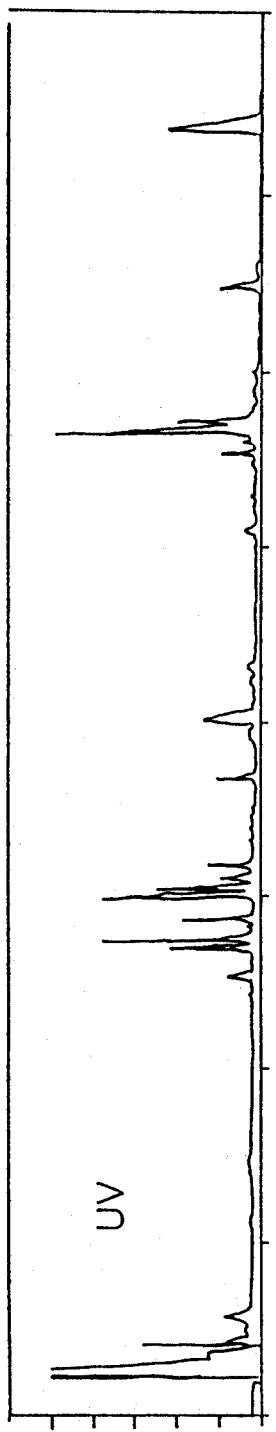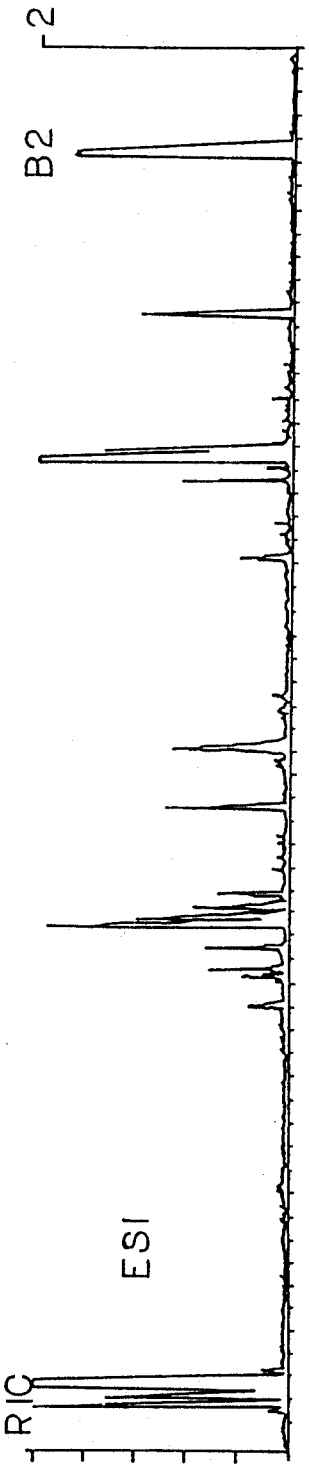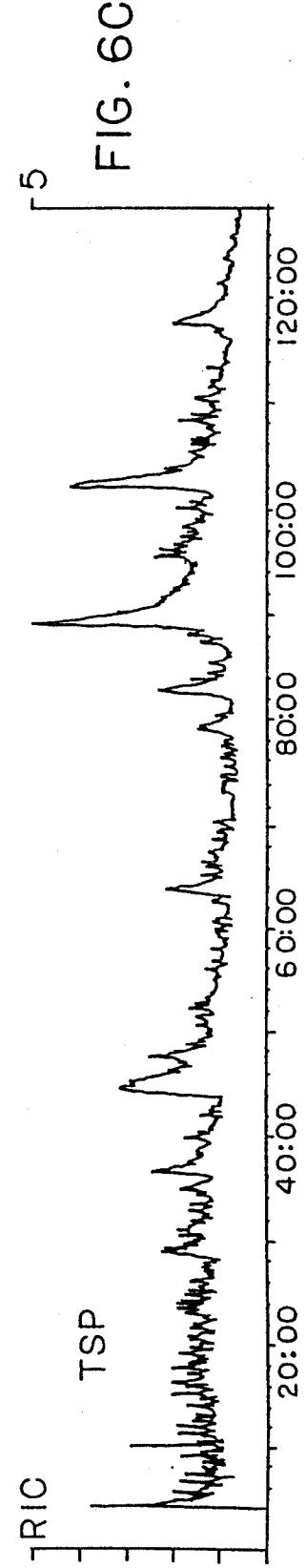
HPLC TRYPTIC MAP OF RECOMBINANT PORCINE SOMATOTROPI (rPSt) USING UV, ESI/MS AND TSP/MS DETECTION.
FIG. 6A
FIG. 6B
FIG. 6C

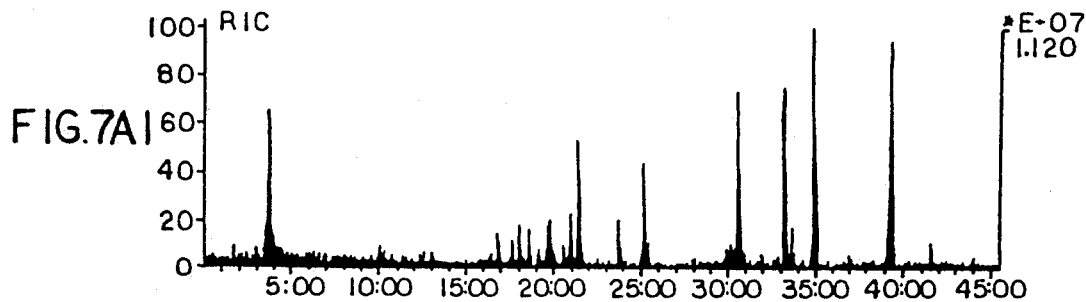
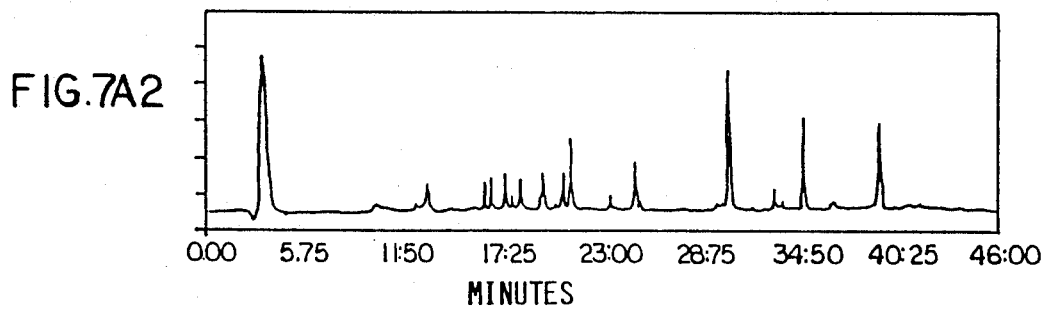
ESI/LC/MS TRYPTIC MAP OF RECOMBINANT BOVINE SOMATOTROPIN (rBSt)
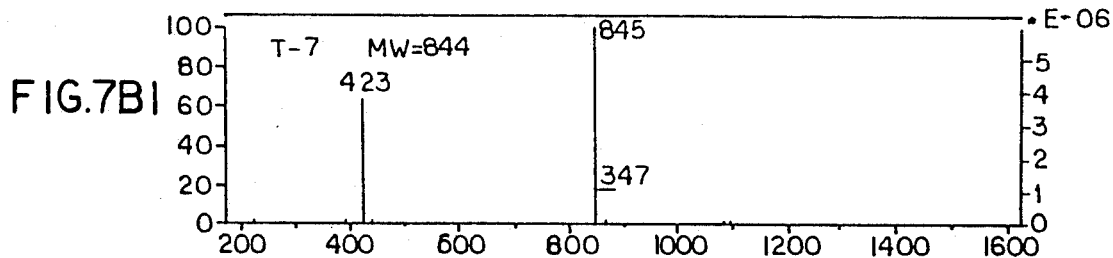
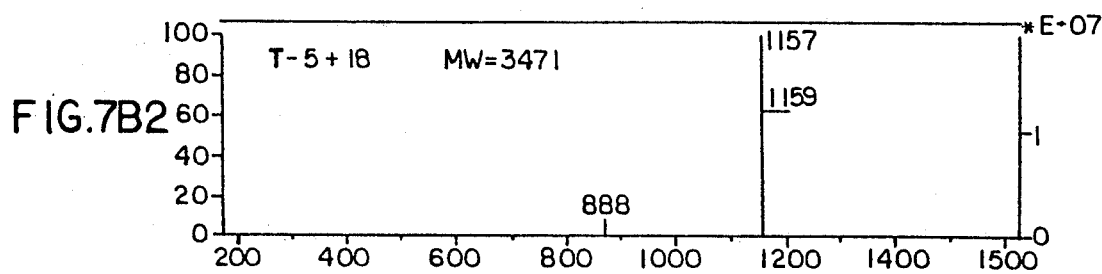
ESI/LC/MS MASS SPECTRA OF rBSt TRYPTIC FRAGMENTS T7 AND T5+18

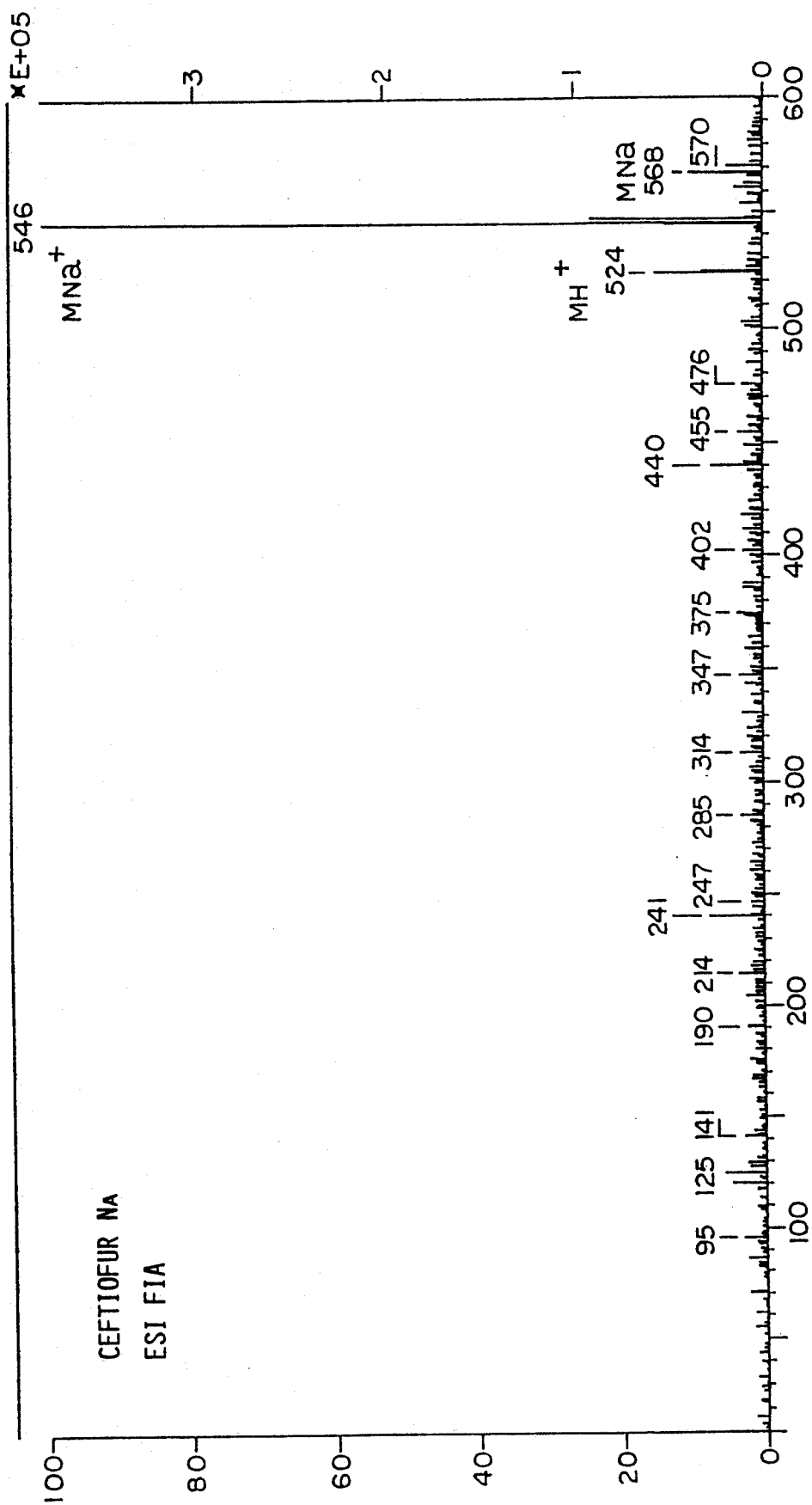

ESI/LC/MS ANALYSIS OF CEFTIOFUR SODIUM IRM

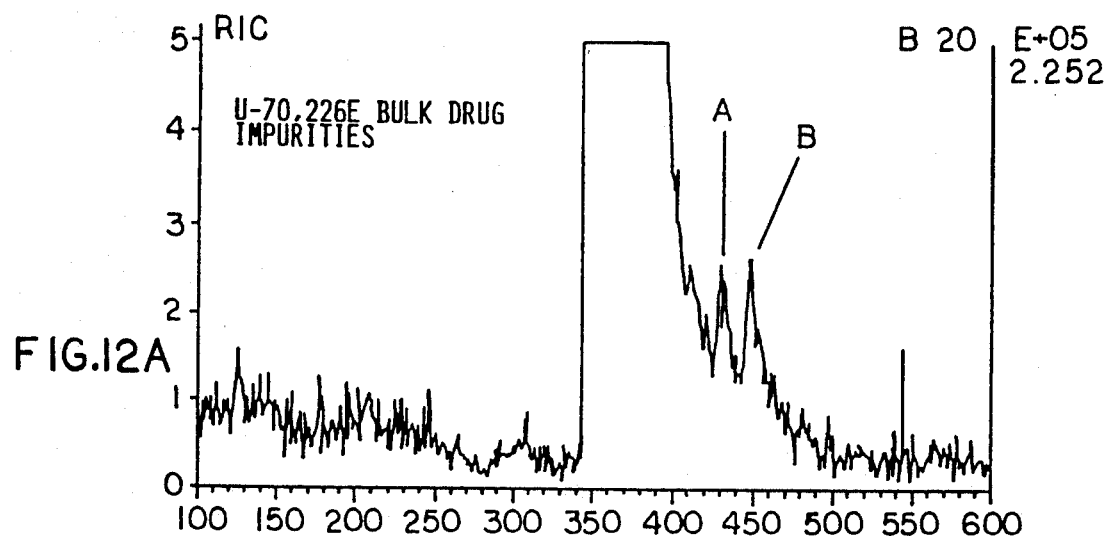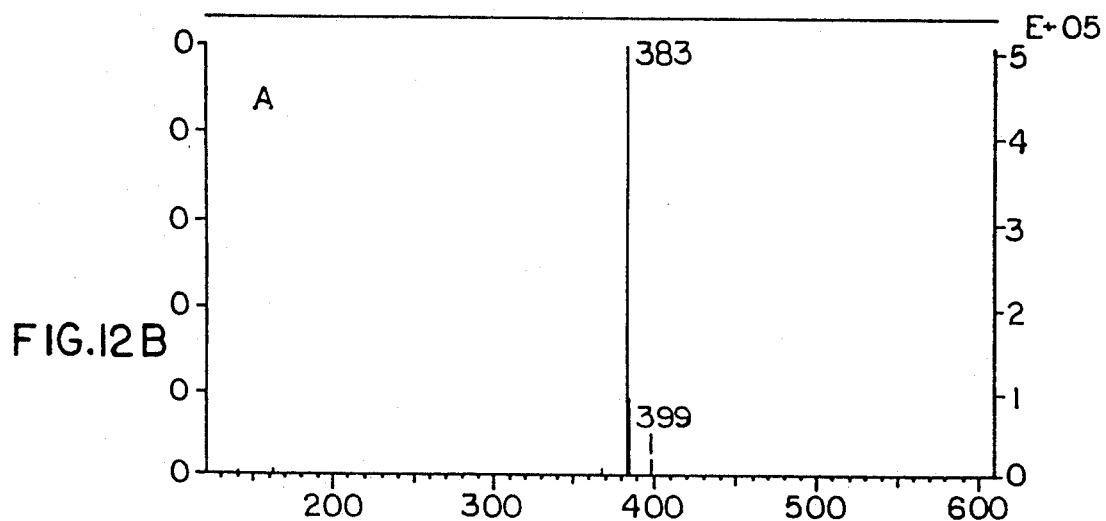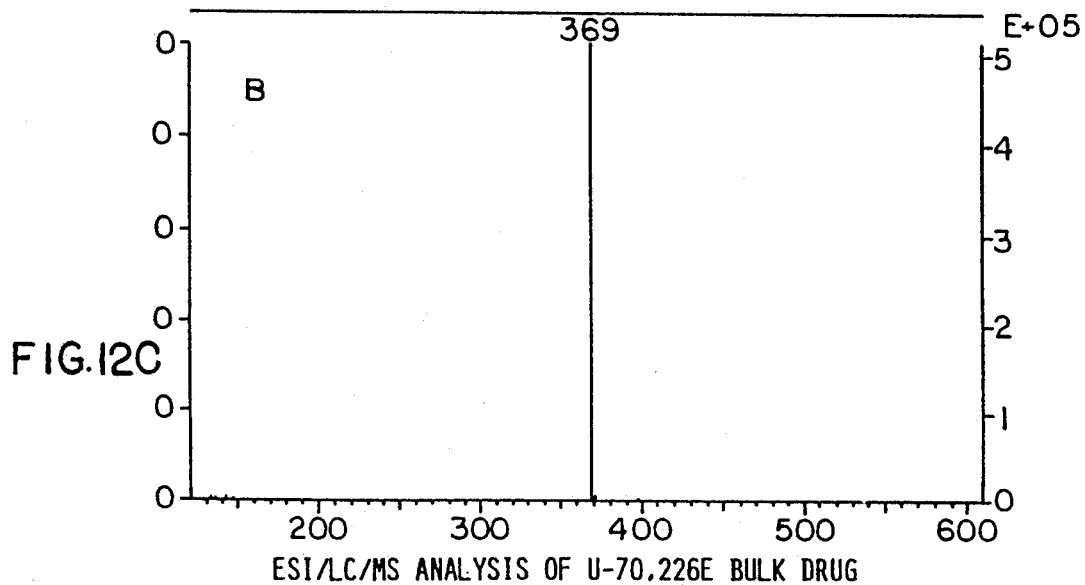
ESI/LC/MS ANALYSIS OF U-70,226E BULK DRUG

ESI/LC/MS SENSITIVITY AND LINEARITY FOR U-70,226E

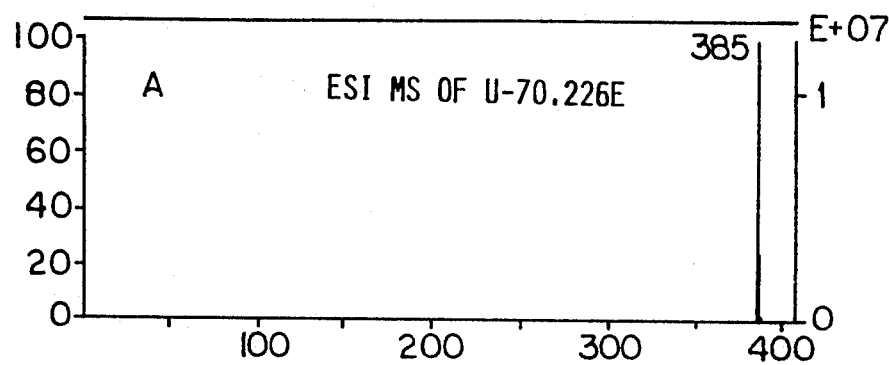
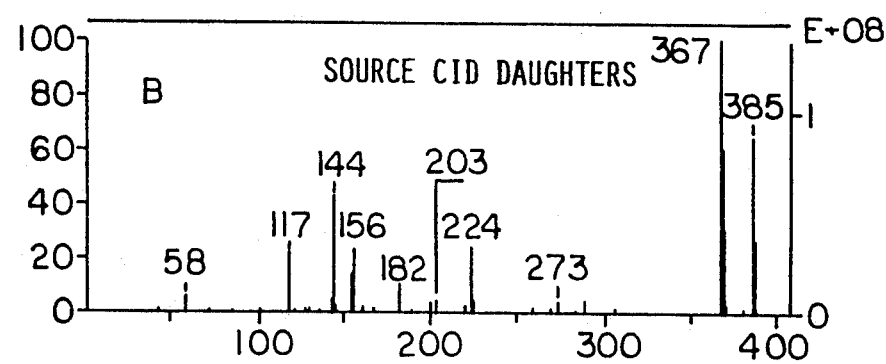
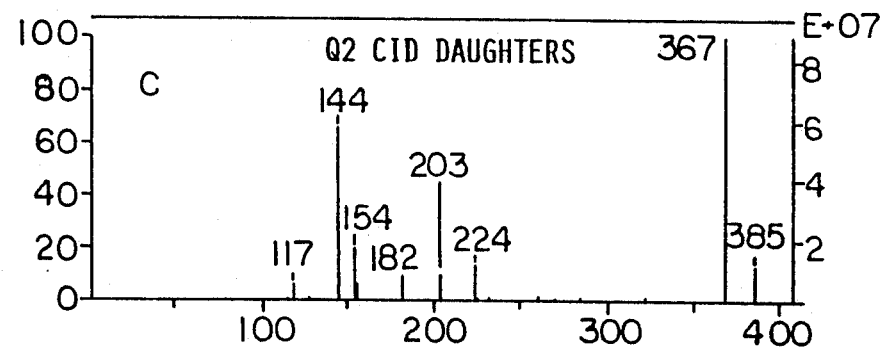
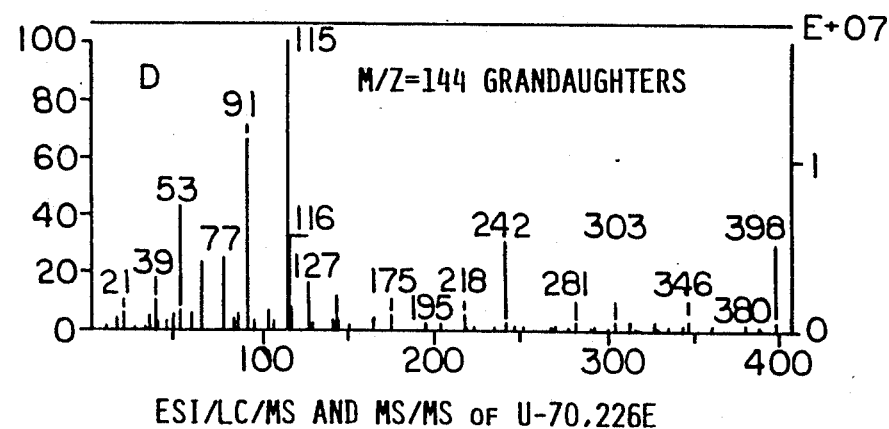
ESI/LC/MS AND MS/MS OF U-70,226E

ESI/LC/MS AND MS/MS OF U-87,201E

PROBE-BASED ELECTROSPRAY ADAPTER FOR THERMOSPRAY EQUIPPED QUADRUPOLE BASED LC/MS SYSTEMS

FIELD OF THE INVENTION

This invention relates to a probe adapter for converting a thermospray equipped quadrupole based LC/MS analyzer to an electrospray equipped quadrupole LC/MS analyzer and, more particularly, to a novel probe-based electrospray adapter for use in conjunction with a thermospray equipped quadrupole based LC/MS analyzer.

BACKGROUND OF THE INVENTION

Maturation of the biochemical field has imposed demands on mass spectrometry (MS) for the analysis of increasingly large and complex biopolymers. Although spectrometer technology has profited from the electronics and computer revolution, two fundamental limitations remain. Analytes of interest must be presented as gas phase ions and their mass to charge ratio (m/z) must be within the instrumental mass range. While increasing mass range is relatively straight forward, producing gas phase ions of polar, nonvolatile and thermally fragile molecules is not.

With the exception of the now nearly abandoned method of Field Desorption (FD), most biomolecule ionization schemes are based on the application of tremendous energy in a short time period. These "energy sudden" methods such as Fast Atom Bombardment (FAB), Laser desorption (LD) and Plasma Desorption (PD), rely on power density to affect sample volatilization/ionization and analysis prior to analyte decomposition. While effective, these methods predominately produce singly charged ions, the analysis of which remains limited by the mass range of common multipurpose sector and quadrupole spectrometers. Further, the transient nature of the ion signal and/or the sample matrix requirements limit or preclude their application to on-line Liquid Chromatography Mass Spectrometry LC/MS.

Electrospray Ionization (ESI) is the latest development in LC/MS interfacing and one which addresses both the ionization and mass range problems. Like Thermospray (TSP), it is a soft spray ionization technique predicated on field induced "ion evaporation" from the surface of charged liquid droplets. Both techniques nebulize the analyte containing semi-aqueous mobile phase to form an aerosol of submicron droplets from which ion evaporation occurs. ESI differs from TSP in three respects;

1) The aerosol is generated electrostatically rather than thermo-pneumatically.

2) Nebulization/ionization is performed at atmospheric rather than reduced pressure.

3) Electrostatic nebulization limits flow rates to ca. 1 to 50 mcl/min.

These differences give ESI its inherently high ionization efficiency and hence mass sensitivity, its ability to produce large gas phase ions of very high charge state (m/z within instrumental mass range), and dictate the low flow regime in which the technique operates.

The current monumental interest in ESI is ironic considering it is the chronological predecessor of most of the energy sudden ionization "breakthroughs" developed over the past twenty years. While electrostatic aerosol generation is not new and has had numerous industrial applications, it was not applied to mass spectrometry until 1968 by M. Dole and others. M. Dole's interest in "macro-ions" of synthetic polymers and adherence to the now rejected "ion residue" model lead to his expectation of large singly charged ions beyond the mass range of analyzers of the day. For this reason, he examined energy analysis for mass determination. Unfortunately, due to the focus of his research, his choice of mass analyzer, and the comparative infancy of biochemistry, the implications of his "discovery" were not recognized by the MS community.

In the late seventies, M. L. Vestal and coworkers discovered TSP while investigating direct thermal LC/MS interfacing methods in ignorance of M. Dole's work. TSP produces charged droplets based solely on statistical charge segregation of buffer/analyte ions manifesting horrendously poor ionization efficiency. Although TSP sensitivity was viewed by many as inadequate for useful biopolymer applications, it did demonstrate the ability to produce ions of these species and with higher charge states. The current ion evaporation model was subsequently proposed.

The success of TSP and the need for higher ionization efficiency (sensitivity) led J. B. Fenn, C. M. Whitehouse and others in the mid eighties to reexamine M. Dole's electrostatic nebulization. Their focus on biopolymers and the availability of compatible high gas load quadrupole spectrometers met with immediate success and ESI became the latest MS bioanalytical bombshell. Commercial ESI interface designs were soon available. The interest in ESI is now immense as evidenced by the 1991 meeting of the American Society of Mass Spectrometry (ASMS) in which there were more than 100 presentations on ESI alone.

All ESI interface designs perform two basic functions; the electrostatic generation of an aerosol at atmospheric pressure from which gas phase analyte ions are produced by ion evaporation and the conveyance of these ions to the high vacuum of the spectrometer. Most designs only differ significantly in how the latter is accomplished.

Electrostatic aerosol generation differentiates ESI from TSP and accounts for most of its unique performance. Depending on the chromatographic scale, all or a fraction (1 to 50 mcl/min) of the semi-aqueous LC eluent is passed through a narrow stainless steel capillary "needle" held at 2 to 4 kV relative to a reference plate. Typically 28 to 33 gauge hypodermic needle stock is used for the capillary with the reference plate being the interface housing itself. Reverse configurations placing high voltage on the reference plate while grounding the needle have also been constructed to minimize electrical complications with chromatographic hardware. It is only important that the relative sense of the needle potential be the same as the ions to be generated.

The intense electrostatic field gradient established between the needle and reference plate is of maximum intensity at the needle tip, approximated by a point electrode. The net electrostatic forces acting on solution state ions elongates the emanating droplet to form a "Taylor" cone. For example, with positive ion MS, solution state cations are attracted toward the relatively negative ground plate while anionic species are electrochemically neutralized at the needle surface leaving predominately cations in the Taylor cone. In this respect, ESI provides charge pumping.

Electrostatic force draws the cone apex into a charged fluid filament a few microns in diameter. Electrostatic repulsion causes ion migration to the filament surface. As the applied field strength decreases with distance from the needle tip, ionic repulsion overcomes surface tension, dispersing the filament into an aerosol of submicron highly charged droplets. The nature of this mechanism dictates that droplets are formed at or near the Raleigh limit—the point at which surface charge repulsion is balanced by surface tension.

Droplets so formed are desolvated as they traverse the atmospheric pressure region between the needle and plate with the heat of vaporization efficiently provided by the ambient gas. Desolvation reduces droplet radii creating surface field strengths above the Raleigh limit. Droplets undergo a "coulombic explosion" to form secondary hyperfine charged droplets and to re-establish equilibrium. Many cycles of this desolvation/fragmentation process produce minute droplets of high net charge. These processes have recently been confirmed by high speed laser photography.

The near point charge concentration of the final droplets may be viewed as Field Desorption emitters. Surface field strengths well into the kilovolt range have been calculated. Solution analyte ions at the surface of these droplets are ejected directly into gas phase when electrostatic repulsion exceeds the solvation energy. This process is referred to as Ion Evaporation.

Although both ESI and TSP produce gas phase ions by ion evaporation, ESI is differentiated from its predecessor TSP by electrostatic aerosol generation at atmospheric pressure. TSP produces an aerosol by partial thermal vaporization of the mobile phase (flow rates 0.5 to 3.0 ml/min) in a metal capillary. Droplets are produced by the pneumatic expansion of the liquid/vapor exiting the capillary tip into a reduced pressure (10–50 torr) source region. Net charging of TSP droplets relies on the random statistical segregation of solution buffer and analyte ions in individual droplets. Both cationic and anionic droplets are produced with ensemble neutrality. Electrostatic charging is not viable at low pressure due to the early onset of corona.

TSP nebulization produces droplets of larger initial radius and much lower net charge as predicted by common sense and proven by Faraday current measurements. Initial droplets are produced well below the Raleigh limit requiring significant desolvation to induce coulombic fragmentation and ion evaporation. Adiabatic expansion and evaporative cooling in the reduced pressure source arrests droplet desolvation requiring copious heating of the TSP source block. Poor thermal contact at low pressure limits desolvation. Low initial charging and incomplete droplet desolvation make the ionization efficiency and hence sensitivity of TSP markedly lower than ESI.

Atmospheric aerosol generation in ESI has ramifications beyond providing the heat of vaporization. The translational, rotational and internal energies of the resulting gas phase ions are defined by the temperature of the ambient bath gas. In this region, energetically "cold" evaporated ions do not participate in ion/molecule processes in the conventional sense. Although Atmospheric Pressure Chemical Ionization (APCI) is well known and useful, it is initiated by very energetic corona or plasma primary ionization with analyte ionization by energy transfer occurring within microseconds during thermalization. Evaporated ions do not possess this initial energy. The influence on this mechanism is not well understood for ESI, but remains important. The higher charge state of ESI ions likely results from the initial charge pumping of the aerosol droplets as well as the inability of these ions to lose charge to thermalized collision partners at atmospheric pressure.

ESI also produces little matrix background from mobile phase constituents. The intense solvent/buffer ion clusters associated with TSP are not observed because their formation mechanism may be restricted by ion evaporation at high pressure. The reduction of chemical interference from the mobile phase is equally as important as the inherent ionization efficiency of ESI. Combined, the two yield a signal-to-noise enhancement of greater than 1000 over TSP on a mass flux basis. This performance is mandatory for successful interfacing to conventional (ml/min) HPLC systems because most of these gains are offset by the requisite splitting of the column eluent. TSP consumes the entire HPLC eluent.

The ESI interface performs three basic functions; 1) It defines the aerosol generation chamber and maintains the electrostatic and thermal conditions needed for efficient and stable ion production. 2) It provides for "declustering" of adducted solvent molecules from gas phase analyte ions. 3) It conveys analyte ions from atmospheric pressure to the high vacuum of the mass analyzer. To accomplish these, two basic interface designs have emerged; the coaxial conical skimmer and the coaxial capillary drift tube. Both designs rely on momentum separation to enrich heavier analyte ions from lighter atmospheric bath gas constituents.

The conical skimmer scheme has existed for decades having been initially developed for high energy corona and plasma APCI applications. A series of two or more conical skimmer cones are arranged behind a forward aperture and coaxial with the gas flow to form the momentum separator. A cylindrical tube about the forward plate defines the aerosol volume. The aerosol volume and the separator are heated independently.

With ESI, the forward aperture plate acts as the planar counter electrode to the aerosol needle. Dry nitrogen curtain gas is heated as it passes between the forward plate and the first skimmer and emerges countercurrent to the aerosol flow. This "drying gas" promotes desolvation of the aerosol droplets and declustering of adducted solvent molecules from evaporated analyte ions. Analyte ions and ambient bath gas are drawn into the first skimmer by instrument vacuum with the pressure between the skimmers reduced by mechanical rotary pumps. Heavier analyte ions maintain their trajectory through the skimmers to enter the mass analyzer while lighter mobile phase and bath gas species are collisionally scattered and pumped away. Voltage placed on the skimmer cones may be used to achieve collisional activation in this reduced pressure region. In addition to diffusion or turbomolecular pumping, cryopumping is employed to achieve a final analyzer vacuum of ca. $10^{-6}$ torr.

Considerable research went into the optimization of skimmer cone geometry and placement with respect to the expansion mach cone in order to maximize ion transmission. A highly successful design of J. A. Buckley et al (U.S. Pat. No. 4 148 196), developed at the University of Toronto, is marketed by SCIEX Ltd. of Canada as an integral component of their quadrupole APCI systems. These systems offer excellent ESI performance. The disadvantages of the design are that it is a relatively complex and dedicated system with inordinately large pumping requirements.

The capillary drift tube design is functionally identical with the aerosol volume and forward aperture plate being similarly constructed. Analyte ions and bath gas are drawn into the interface by instrument vacuum via a heated metal or metalized fused silica capillary drift tube located concentrically within the forward aperture. Countercurrent drying gas is introduced between the capillary and forward aperture for the same purpose as before. Ions traversing the 20 cm by 0.5 mm ID capillary are thermally declustered before entering the single stage mechanically pumped momentum separator. Heavier analyte ions are again conveyed to the analyzer via a single skimmer cone while lighter solvent and bath gas species are pumped away. Bias voltage placed on the capillary accelerates ions exiting the drift tube to provide collisional activation within the skimmer region. Gas flow into the interface is limited by the conductance of the drift tube such that conventional diffusion or turbomolecular analyzer pumping is adequate.

The design of Fenn, Meng and Mann (WO90/14148) has been commercially implemented on Finnigan quadrupole spectrometer systems. Chowdhury, Katta and Chait have incorporated a similar design (U.S. Pat. No. 4 977 320) on Hewlett-Packard MSD bench top systems which does not make use of the drying gas. Both devices have demonstrated admirable ESI performance. These designs have the advantage of simplicity and reduced pumping requirements, however, they remain integral components requiring significant modification and hence near dedication of the spectrometer.

The uniqueness of ESI as a primary ionization method and as an LC/MS interface make its application to pharmaceutical development problems highly desirable. Due to the high cost and instrumental dedication required by commercially available devises, the development of a simple, cost effective, yet functional interface more amenable to the multi-mode research MS environment was undertaken. The provision of a simple probe based ESI interface system fulfilling these requirements is the subject matter of this invention.

Accordingly, it is an object of this invention to provide a device for facilitating the conversion of a thermospray equipped mass spectrometry analyzer to one capable of using electrospray technology without necessitating a removal of the thermospray equipment.

It is a further object of this invention to provide a probe-based electrospray adapter for use in converting a thermospray equipped quadrupole based LC/MS analyzer to an analyzer capable of receiving ions created by electrospray ionization technology.

It is a further object of this invention to provide a probe, as aforesaid, capable of use with an existing thermospray equipped LC/MS analyzer without complicated changes being required to the analyzer to thereby facilitate a continued and convenient use of all instrument capabilities at a subsequent time.

It is a further object of this invention to provide a probe, as aforesaid, which has adjustable features on it that can enhance the responsiveness of the analyzer, which adjustment features are independent of structure of the analyzer.

It is a further object of this invention to provide a probe, as aforesaid, which is inexpensive to manufacture, easy to operate and easy to maintain in proper operative condition to achieve high quality results from the analyzer.

SUMMARY OF THE INVENTION

The objects and purposes of the invention are met by providing a probe adapter for converting a thermospray equipped LC/MS analyzer to an electrospray equipped LC/MS analyzer. The probe adapter includes structure defining an elongated and hollow first chamber opened at one end to atmosphere and closed at the other end by a first partition. Additional structure is provided defining a hole through the first partition and an elongated and hollow probe shaft is connected to and extends from the first partition on a side thereof remote from the opened end. A central axis of the probe shaft is coaxial with a central axis of the first hole. A second partition is provided in the first chamber and is spaced from the first partition and defines a second chamber therebetween. Adjusting structure is provided for selectively adjusting the spacing between the two partitions. A second hole is provided in the second partition and is coaxially aligned with the first hole. An elongated and hollow drift tube is mounted inside the probe shaft, an inlet end of the drift tube extending through the first hole in the first partition and terminating in the second chamber. An outlet end of the drift tube extends a finite distance beyond an end of the probe shaft remote from the first partition. The relative spacing between the first and second partitions determines a spacing between the inlet end of the drift tube and the second hole.

BRIEF DESCRIPTION OF THE DRAWINGS

Other objects and purposes of this invention will be apparent to persons acquainted with apparatus of this general type upon reading the following specification and inspecting the accompanying drawings, in which:

FIG. 2 is a longitudinal, partially exploded, sectional view through the center of my probe and accompanying electrospray needle, the internal mechanism of the mass spectrometer to which my probe is connected being shown schematically;

FIG. 2A is an enlarged fragment of a portion of my probe illustrated in FIG. 2;

FIG. 3 is a sectional view taken along the line 3—3 of FIG. 2;

FIGS. 4-15 illustrate various electrospray ionization mass spectra of various compounds, which spectra were acquired utilizing my probe-based electrospray adapter.

DETAILED DESCRIPTION

Figure 1:
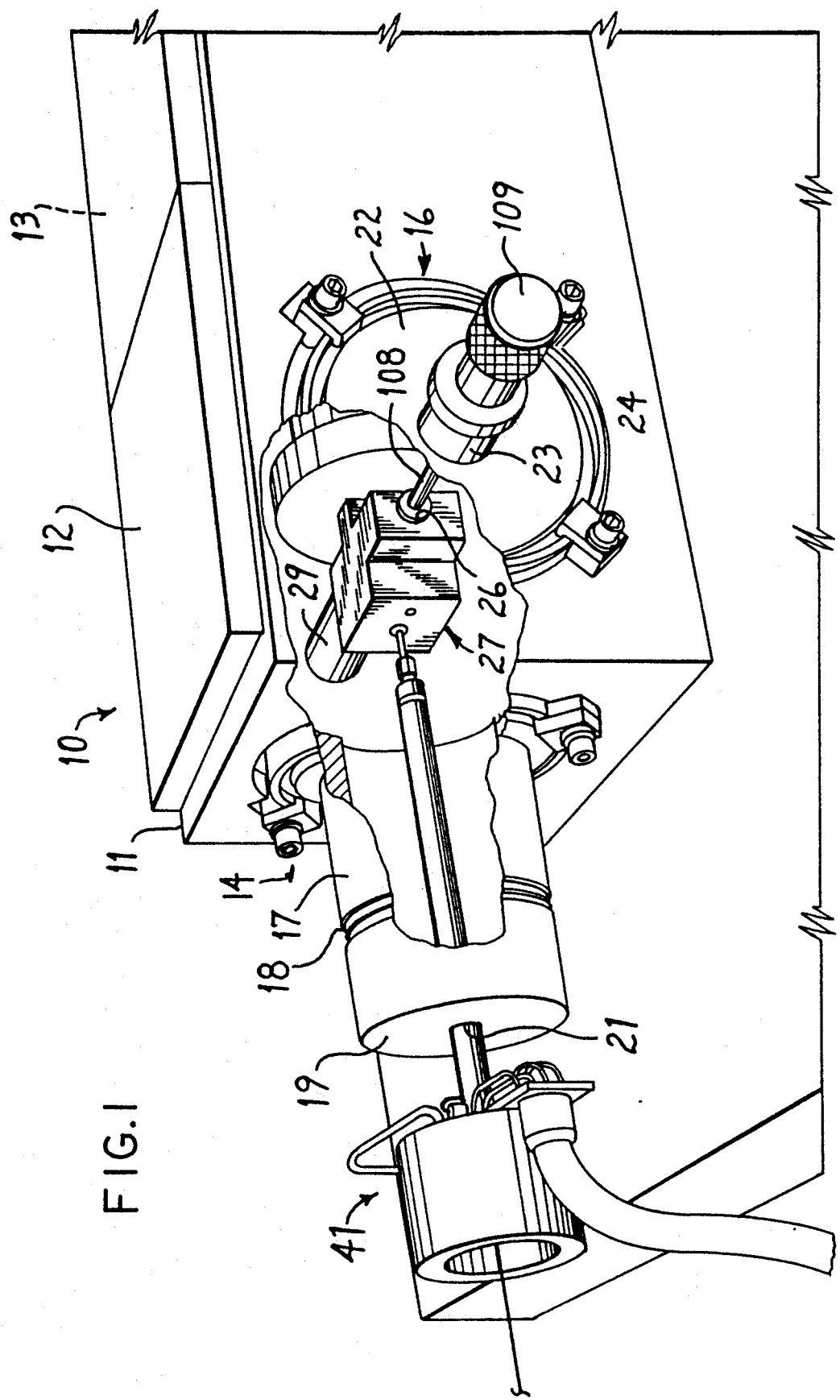
FIG. 1 is an isometric view of an existing mass spectrometry analyzer having my probe-based electrospray adapter which embodies the invention shown in association therewith.
Figure 5:
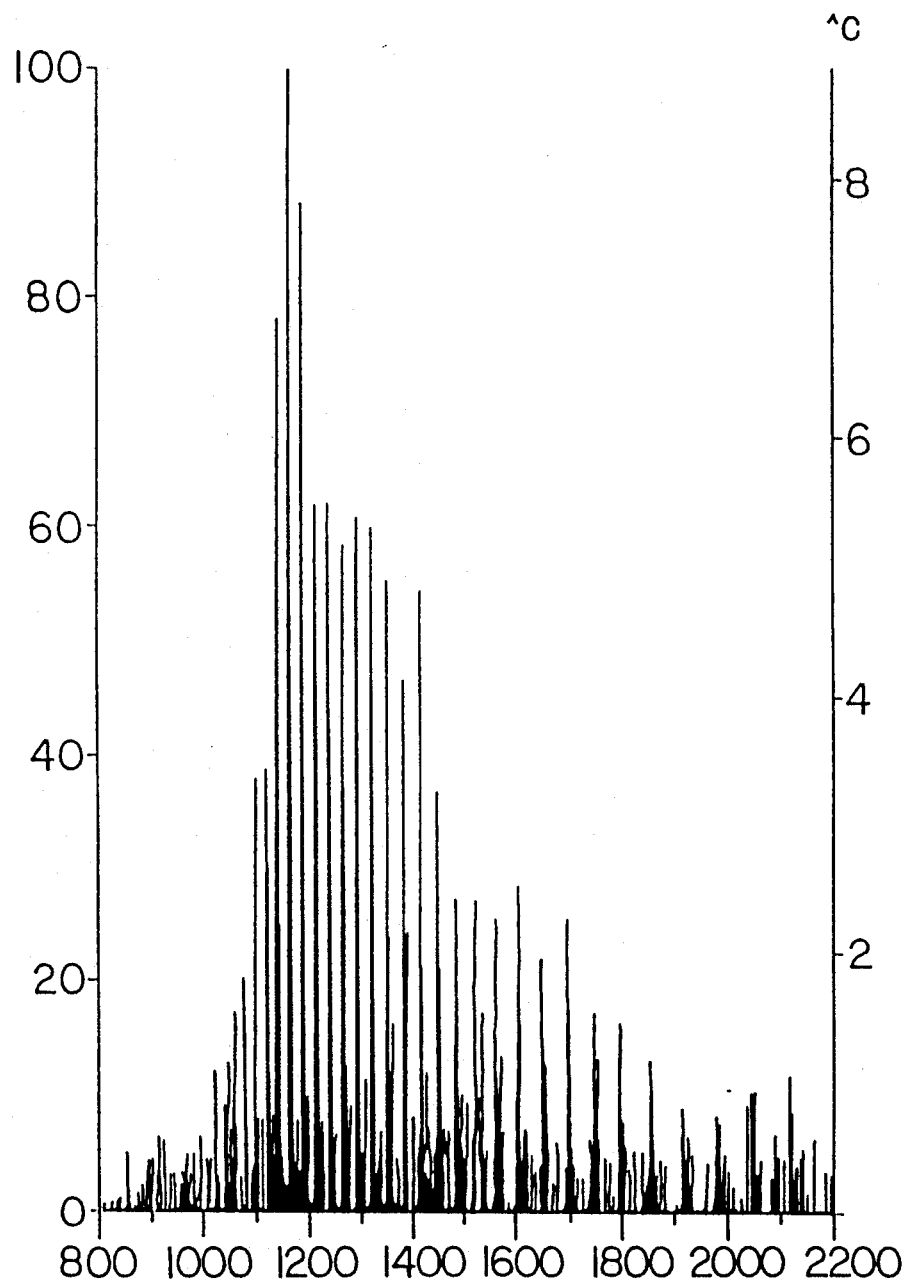

Certain terminology will be used in the following description for convenience in reference only and will not be limiting. The words "up", "down", "right" and "left" will designate directions in the drawings to which reference is made. The words "in" and "out" will refer to directions toward and away from, respectively, the geometric center of the device and designated parts thereof. Such terminology will include derivatives and words of similar import.

FIG. 1 illustrates an existing thermospray equipped quadrupole based LC/MS analyzer, particularly a Finnigan TSQ series quadrupole spectrometer. All data reported below and shown in FIGS. 4-15 were acquired using a TSQ-70 triple quadrupole spectrometer with an associated U.S. Designs VIP 1173 data system running ICIS rev 5.0 software. The analyzer has been identified generally by the reference numeral 10. The analyzer 10 includes a housing 11 and a variety of airtight, sealed access panels 12 and 13 which are removable to allow access to the interior of the housing 11. As shown in FIG. 1, a pair of airlocks 14 and 16 also provide access to the interior of the housing 11. The airlock 14 has a cylindrical member projecting away from the housing 11 to an opened end 18 closed by a cover 19 having in an end wall surface thereof an opening 21 that can be closed off by means of an internal ball valve assembly not illustrated. The airlock 16 has an opening extending through a plate 22, which opening communicates with a hollow tubular member 23 projecting away from the plate 22 and terminating at an end thereof remote from the plate 22 in an opened end 24, which opened end provides access through the tubular member 23 to the interior of the housing 11. In thermospray ionization technology, the liquid chromatograph (LC) eluent is vaporized by a liquid vaporizer (not shown) and conveyed into the open end 24 of the tubular member 23 and delivered to an inlet opening 26 of a thermospray ion source body 27. The outlet opening 28 (FIG. 2) from the thermospray ion source body 27 is connected through a tube 29 to a vacuum source P capable of generating a vacuum for analyzer pressure below $3 \times 10^{-5}$ torr. It is preferable, however, that the vacuum source P be capable of generating vacuums below 20 torr within the passageway 31 between the inlet opening 26 and the outlet opening 28 of the thermospray ion source body 27. A conventional skimmer cone 32 having an inlet orifice 33 extending therethrough as well as the quadrupole and lens system schematically represented by the reference character 34 are provided in the mass spectrum analyzer 10.

All of the structure described above with respect to the analyzer 10 is known and does not form a part of the invention. What is, however, deemed to be new and novel is my probe-based electrospray adapter generally indicated by the reference numeral 41. The probe adapter 41 includes a generally cup-shaped housing member 42 having a generally hollow cylindrical wall 43 opened to the atmosphere at one end 44 and closed at the other end by a wall 46 defining an end surface 47. A plurality of blind holes 48 are provided in the end surface 47 adjacent the perimeter of the cylindrical wall 43, which holes have a sufficient depth to virtually extend the length of the cylindrical wall 43, but yet be isolated from the end of the cylindrical wall 43 adjacent the opened end 44. An electrical heater element 49 is received in each hole 48. Electrical wiring 51 for controlling the amount of electrical energy fed to the heater elements 49 extends outwardly from the surface 47 as shown in FIG. 2.

In this particular embodiment, the end wall 46 has a central hole extending therethrough. The end of the hole 52 adjacent the surface 47 is countersunk and an internal thread 53 is provided on the radially inwardly facing surface thereof. The countersunk hole is coaxial with the hole 52. A pair of additional holes 54 are provided in the end wall 46 and extend completely through the wall. The holes 54 are diametrically spaced from one another and on opposite sides of the central hole 52.

The interior of the housing 42 includes a cylindrical radially inwardly facing surface 56. A disk or plate 57 having a central hole 58 therethrough is received in the open end 44 of the housing 42 with the peripheral edge surface of the plate 57 slidably engaging the radially inwardly facing surface 56. A pair of stud bolts 59 are secured to the plate 57 on a side thereof facing the end wall 46, are aligned with the holes 54 and are received through the holes 54 as shown in FIG. 2. The ends of the stud bolts 59 are externally threaded as at 61, which externally threaded ends are each adapted to be operatively engaged by a nut 62. An O-ring 63 is provided outboard of the stud bolts 59 between the plate 57 and the end wall 46. The O-ring 63 is of a compressible nature so that when the nuts 62 are threadedly mounted on the external thread 61 of each of the stud bolts 59 and tightened, the O-ring 63 will be compressed between the opposing surfaces of the plate 57 and the end wall 46.

An elongated and hollow probe shaft 66 includes at one end thereof, here the left end 67, an external thread 68 which threadedly engages the internal thread 53 in the countersunk hole in the end wall 46. The probe shaft 66 extends away from the end wall 46 in a direction generally perpendicular to the plane defined by the end surface 47. The exterior surface of the probe shaft 66 is polished to produce a smooth finish for smooth operation in the existing spectrometer airlock 14 as will be explained in more detail below. The hollow interior of the probe shaft 66 includes an elongated drift tube 69 which has a length greater than the length of the probe shaft so that the ends thereof project from opposite ends of the probe shaft 66. In this embodiment, the drift tube 69 is 25 cm long by 0.5 mm ID stainless steel. The drift tube 69 extends through the central region of the probe shaft and is held in the central region of the probe shaft by the fact that the left inlet end 88 of the drift tube 69 is received in the hole 52 and projects a finite distance beyond the end wall 47 into a chamber 71 defined between the end wall 46 and the plate 57. The right outlet end 89 of the drift tube is centrally oriented with respect to the probe shaft 66 by an end plug 72 having a central opening 73 therethrough through which is received the right outlet end of the drift tube 69. The plug 72 is welded to the probe shaft 66 so as to define a vacuum seal. A graphite ferrule 74 and a compression nut 76 are provided to further enhance the electrical connection and continuity of the drift tube to the probe shaft. A heater support tube 77 encircles the drift tube 69. The plug 72 serves to maintain the concentric relation between the right end of the drift tube 69 and the right end of the heater support tube 77. A fiberglass electrical insulating tape 79 is wrapped around the exterior of the heater support tube 77. A thermocouple 81 is embedded within the tape 79 as shown in FIG. 2A. Heater wires 82 are next wrapped around the insulation tape 79. The heater wires 82 extend substantially the length of the heater support tube 77 as shown in FIG. 2. Electrical wiring supplying energy to the heater wires 82 is shown at 83 in FIG. 2. Further electrical insulating tape 84 is wrapped around the heater wires 82 to electrically isolate the heater wires 82 from the probe shaft 66 as shown in FIG. 2A. Appropriate passageways 86 defined by holes extending through cylindrical sleeves 87 facilitate communication between the exterior of the probe shaft 86 and the interior thereof to further facilitate the passage of electrical wires 83 therethrough as shown in FIG. 2. The assemblage of heater support tube 77, electrically insulative tape 79 and 84 and heater wire 82 are packed into the probe shaft 66 so as to define a unit separate from the drift tube 69.

The inlet end 88 to the drift tube 69 is coaxially oriented close to and, in some instances, within the confines of the hole 58 in the plate 57 so that only a few thousandths clearance exists between the inlet end of the drift tube 69 and the internally facing surface of the hole 58. The outlet end 89 is adapted to be received through a central hole 91 in an electrically insulative sleeve 92, which sleeve 92 is received in the existing repeller port 93 in the thermospray ion source body 27. The outlet end 89 of the drift tube 69 communicates freely with the passageway 31 and is coaxially aligned with the inlet orifice 33 in the skimmer cone 32. The thermospray filament ionization electron entrance hole (not shown) is not used in the particular embodiment and is sealed by any convenient means, such as silver solder. The thermospray aerosol thermocouple port 94 is sealed with a press fit plug 96.

The housing 42 has a further hole 97 provided through the end wall 46, one end of the hole 97 adjacent the surface 47 being internally threaded as at 98. The hole 97 is adapted to receive therein tubing 99. A compression sleeve 101 encircles the tubing and an appropriate externally threaded plug 102 having a central hole therethrough, through which the tubing 99 extends, is threadedly engaged into the hole 97 so as to sealingly compress the compression sleeve 101 between the internal wall of the hole 97 and the external surface of the tubing 99. The tubing 99 is connected to a source of nitrogen drying gas.

An additional thermocouple 103 is mounted on the surface 47 of the end wall 46 and the electrical wires 104 therefor are shown in FIG. 3.

OPERATION

In order to orient my probe adapter 41 to the existing analyzer 10, the inlet opening 26 to the thermospray ion source body 27 is closed by a plug 106 having appropriate seals 107 thereon so that a vacuum can be drawn in the passageway 31 by the vacuum source P. In this particular embodiment, I have utilized, in addition to the plug 106, an elongated rod 108 on the end of a fitting 109 (FIG. 1) adapted to be received into the open end 24 of the tubular member 23 on the plate 22 of the airlock 16. If desired, the fitting 109 can be secured to the tubular member 23 so that the rod 108 will hold the plug 106 in the inlet opening 26 of the thermospray ion source body 27.

Next, the probe shaft 66 is inserted into the opening 21 in the end wall of the cover 19 to the airlock 14 and the outlet end of the drift tube 69 is inserted into the hole 91 provided in the sleeve 92 received in the repeller port 93. A compression sleeve 111 is compressed between an internally facing surface of the opening 21 on the cover 19 and an exterior surface of the probe shaft 66 so as to render the seal airtight. In this particular embodiment, for example, the cover 19 can be threadedly secured to the cylinder housing 17 so that the cover 19 will move toward an end wall 112 of the cylinder housing 17 so that an axially extending flange 113 on the end wall 112 engages the compression sleeve 111 to urge the compression sleeve into a snug and sealed relation with the exterior surface of the probe shaft 66 and the inwardly facing surface of the opening 21. A clearance space 114 can, if desired, be provided between the exterior surface of the probe and an inwardly facing surface of a hole through the end wall 112 around which the aforesaid axially extending flange 113 is oriented.

The housing member 42 on the left end of the probe shaft 66 is supported in a cantilevered manner outwardly away from the cover 19 as shown in FIG. 1. No additional support of the housing 42 is required.

A LC eluent splitter 116 is oriented to the left of the open end 44 to the housing 42 as illustrated in FIG. 2. The splitter 116 includes a housing 117 having a T-shaped passageway system 118 provided therein. An elongated needle 119 is connected to a fitting 121 connected in fluid circuit with one leg of the T-shaped passageway system 118. The needle 119 is generally axially aligned with the orifice 58 in the plate 57 and generally axially aligned with the axis of the drift tube 69. A conduit 122 for supplying LC eluent is connected to a fitting 123 which is connected to the stem of the T-shaped passageway system 118 to supply LC eluent to the passageway system. A further conduit 124 is connected to a fitting 126 which is connected to the other leg of the T-shaped passageway system 118, which leg is axially aligned with the leg connected to the needle 119. The fitting 126 provides fluid communication between the passageway system 118 and the conduit 124. In this particular embodiment, as LC eluent is introduced into the passageway system 118, a small fragment thereof exits the passageway system through the needle 119. A major portion of the LC eluent is delivered to a collection reservoir (not shown) for further use.

An electrical wire is connected to the housing 117 and the power supply so that a voltage in the range of 1800 to 2100 volts can be applied to the housing 117. Since the fitting 121 is preferably electrically conductive as is the needle 119, such voltage will also be effectively applied to the needle 119. Similarly, an electrical wire 128 is connected to the probe shaft 66 and to the power supply. The power supply is adapted to provide a drift tube bias voltage in the range of 0 volts to 300 volts. Additional wiring 129 and 130 is provided for connecting the power supply to the heater elements 49 and 82 so as to heat the housing 43 and the probe shaft 66 to desired temperature limits. Additional wiring, only a fragment 104 being shown in FIG. 3, is provided for connecting the thermocouple 103 to a monitoring device to facilitate a monitoring of the temperature of the housing 43. Similarly, wiring, not shown, is provided for connecting the thermocouple 81 on the probe shaft 66 to a monitoring device to facilitate a monitoring of the temperature of the probe shaft. A drying gas is coupled to the conduit 99 and fed to the chamber 71. In this particular instance, the drying gas is nitrogen.

The following is a listing of the functional range for the various parameters involved in setting up this apparatus as well as a listing of the optimum conditions for operation.

| Parameter | Functional Range | Optimum |
|---|---|---|
| Housing temp: | 50–200 C. | 80 C. |
| Drift tube temp: | 80–250 C. | 200 C. |
| Plate/tube spacing: | 0–4 mm | 2 mm |
| Tube/cone spacing: | 4–10 mm | 4 mm |
| Drying gas flow: | 0–100 ml/min | 50 ml/min |
| Aerosol needle gauge: | 28–33 gauge | 33 gauge |
| Needle voltage: | 1800–2100 volts | 2000 volts |
| Mobile phase flow: | 0.5–10 mcl/min | 2 mcl/min |
| Tube bias voltage: | 0–300 volts | 50 volts |

The electrospray ion (ESI) interface 132 is adjusted so that the free end of the needle 119 is set a predefined distance away from the orifice 58. The inlet end of the drift tube 69 was adjusted in accordance with the plate/tube spacing indicated above. The outlet end 89 of the drift tube 69 was oriented a predetermined spacing from the inlet to the skimmer cone in accordance with the tube/cone spacing indicated above.

The probe shaft 66 and the heater support tube 77, as well as the heater construction provided in the annular space therebetween, form a unit. The drift tube 69 is removably supported in the hollow interior of the heater support tube 77 so that the drift tube 69 can be removed and replaced by merely loosening the cap 76. Also, because bias potential is placed on the drift tube during operation, electrical isolation of the heater 82 is mandatory. Counter winding of the heater wires 82 nullifies magnetic fields induced by the heater current. Additionally, the heater support tube 77 being made of, preferably Ferrous, metal serves to contain heater induced fields within the tube to thereby prevent adverse influence on ion trajectories in the drift tube. Lastly, the heater support tube 77 increases the thermal inertia of the drift tube insuring adequate temperature regulation.

The following ESI/LC/MS data document the basic capabilities of the probe based ESI interface design described. These analyses were not intended to illuminate the full capabilities of the design but to provide a preliminary performance comparison to documented designs in the literature and to assess its utility to common pharmaceutical development applications.

As mentioned, the current interest in ESI arises from the unique ability to produce gas phase ions of high charge state for large biopolymers including intact proteins. FIG. 4 illustrates the chromatographic separation of three intact proteins; cytochrome c (MW=12,384 kDa.), myoglobin (MW=ca. 16 kDa.), and rBSt (MW=21,808). A mixture containing approximately 10 nanomoles of each protein was injected on a Rexchrom C8 (3 cm×4.6 mm) HPLC column and separated using a 0–100 acetonitrile gradient in 30 minutes. Column eluent was conveyed to the interface via the 1:1000 splitter thereby delivering approximately 10 picomoles of each species for mass analysis. The spectrometer was repetitively scan from nm/z=200 to 4000. The resulting reconstructed total ion current (RIC) chromatogram shown exhibits excellent signal-to-noise (S/N) and ion current stability. The minor peaks between "B" and "C" are stranger proteins in the mixture and not the result of ESI instability. The mass spectra shown for the three proteins are not background subtracted and similarly show excellent S/N ratio. The bimodal appearance of the cytochrome and myoglobin spectra result from an inappropriate tune table in which resolution was inadvertently degraded above 1500 amu.

The distribution of multiple charge states is clearly observed in each spectrum. Charge state is readily determined from any two adjacent ions using the expression:

$$n2 = m1 - 1/m2 - m1$$

Where, m1 is the observed mass of the lighter ion, m2 is observed mass of the heavier ion, and n2 is the charge state of ion m2. With the charge state of each ion determined, the molecular weight (M) of the protein is calculated directly by;

$$M = ni \times (mi - 1)$$

Modern MS data systems provide algorithms which directly "reconvolve" this raw MS data such that conventional unit charge mass spectra are presented. Computerized reconvolution allows the molecular weight to be read directly from spectrum and greatly simplifies the detection of multiple components not recognizable by casual observation of the multi-charge spectra.

Similarly, an 8 nmole sample of CD4-PE40 (MW=ca 60 kDa.) was chromatographed using the same system presenting 8 pmoles to the ESI interface via the splitter. The sample required chromatographic desalination of aqueous matrix buffers for successful ESI/MS analysis. The spectrum resulting from a single 30 second scan taken at the apex of the chromatographic peak appears in FIG. 5. Multiply charged pseudo molecular ions of greater than +50 charges are easily observed in the unsubtracted spectrum. These data confirm the ability of the interface to produce highly charged ions of large biopolymers with molar sensitivity equivalent to that of commercial interface designs reported in the literature.

A primary application of TSP/LC/MS has been the analysis of proteolytic digests of proteins. The primary sequence of the protein is confirmed by determining the retention time and molecular weight of the resulting peptide fragments. Although very successful, TSP has been hindered by high background noise, high maintenance requirements, and a strong user dependency. FIG. 6 shows the chromatographic analysis of a tryptic digest of recombinant porcine somatotropin (rPSt) using both TSP and ESI methods. Two nmoles of digest were chromatographed using a Bakerbond C8 wide pore column (4.6 mm×25 cm) and a 0%–70% acetonitrile gradient in 120 minutes.

From the figure, the ESI RIC data faithfully follows the UV chromatogram while many peaks are unrecognizable in the TSP RIC data. The mobile phase background noise, chromatographic fidelity, and ion current stability of the ESI data are markedly better than for TSP. The improved S/N ratio and lower spectral density of the ESI data makes tryptic peaks considerably easier to identify and spectral processing much faster. A ten fold reduction in data analysis time has been experienced for ESI relative to TSP. The latter is significant since data analysis is the most time consuming process in protein mapping by LC/MS.

ESI offers several secondary advantages. The interface consumes only 1/1000th of the LC eluent (2 pmoles) allowing collection of the waste stream for subsequent MS/MS or Edmund sequence analysis. TSP consumes the entire sample. The high solvent burden of TSP requires backing pump cryotrapping. These traps must be serviced after only a few long chromatographic mapping runs and preclude unattended operation of the instrument. Similarly, erosion of the TSP vaporizer and fouling of the TSP source dictates frequent and time consuming servicing of the interface. Proper set-up of the TSP vaporizer and source is tedious and performance is very user dependent. Conversely, the ESI interface operated for over five weeks with out service. Long chromatographic mapping runs could be acquired without the attendance of the operator. This allows ESI/LC/MS methods to be automated and data acquired under autosampler control.

Figures 8A, 8B:
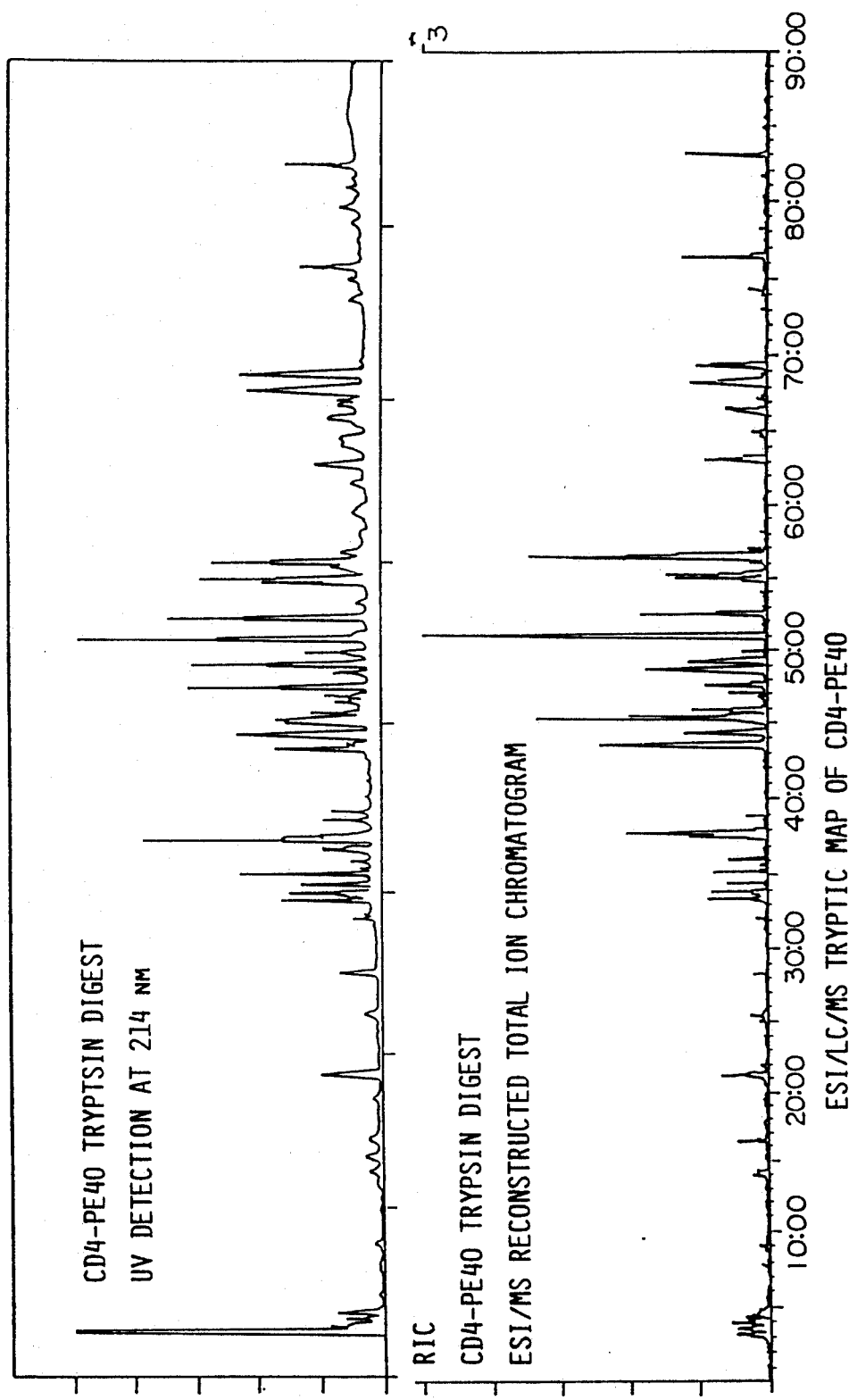

Tryptic mapping of rBSt was likewise performed as shown in FIG. 7. Similar correspondence between the UV and ESI RIC data are observed. The unsubtracted mass spectra of two of the tryptic peptides, T7 and disulfide linked T5+18, are also shown. The spectrum of T7 (MW-844) exhibits a singly charged protonated molecular ion at m/z=845 and doubly charges ion at m/z=423. The spectrum of T5+18 (MW=3471) does not contain singly or doubly charged ions rather, M+3 and M+4 are observed at m/z=1157 and 868 respectively. The S/N ratio of these spectra are excellent at the 2 pmole level. For completeness, the ESI/LC/MS tryptic map of CD4-PE40 is shown in FIG. 8. These data demonstrate the routine use of the ESI interface for protein mapping applications.

Sequence information for small proteolytic peptides may be acquired directly by MS/MS analysis. Ion evaporation methods however, produce primary ions of very low internal energy which are difficult to fragment using the low collisional energy regime of quadrupole instruments. MS/MS sequence analysis of peptides larger than 800 amu has not been effective by TSP. Conversely, for reasons unclear, collisional activation of "energetically cold" multiply charged ESI parent ions yields copious fragmentation from which the sequence can be obtained. The success of peptide ESI/MS/MS sequencing at low collision energy has been attributed to the intramolecular repulsion within the multiply charged parent ions and the proportional extension of the collision energy regime with charge state.

Figure 9:
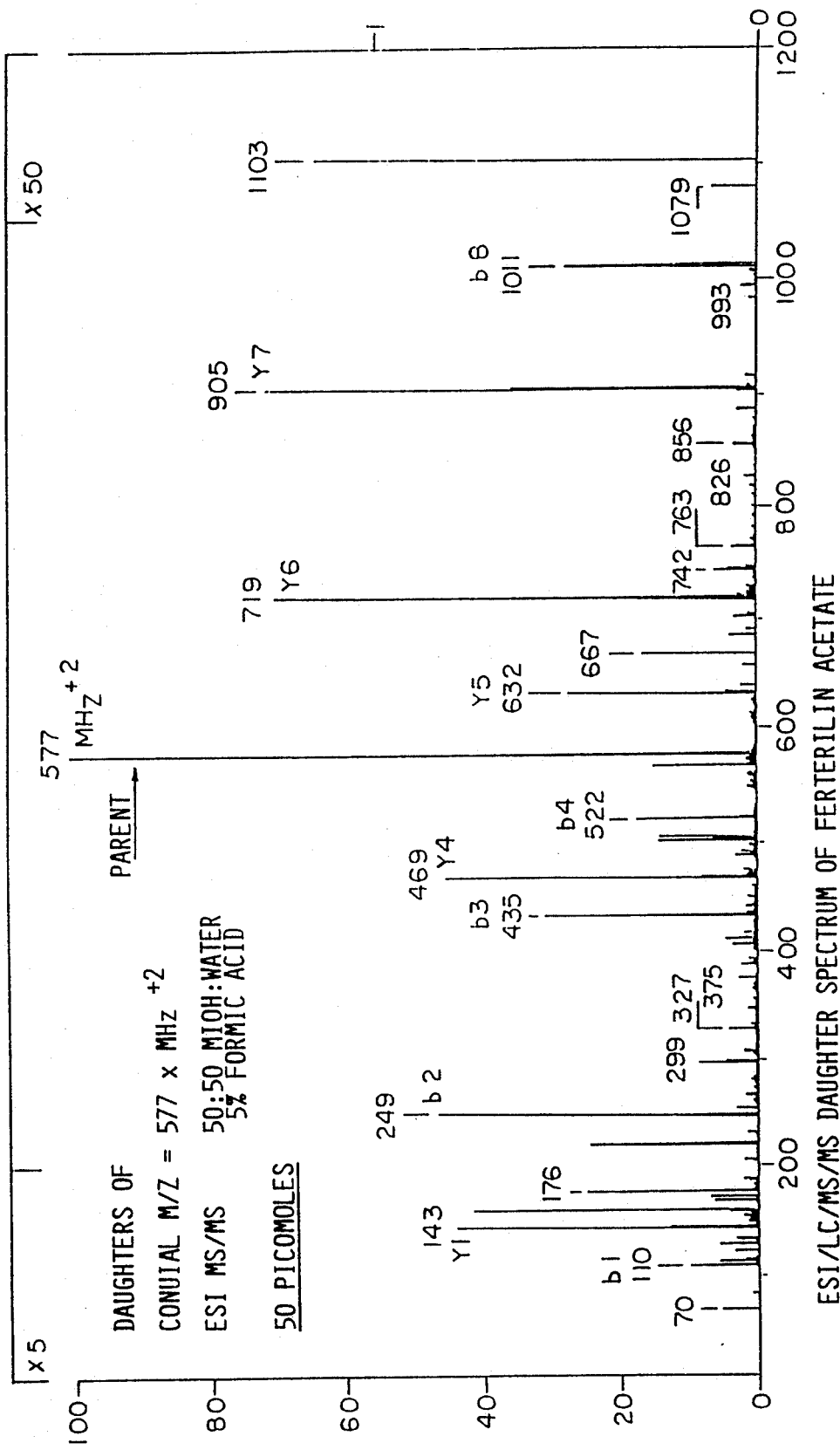
Figure 11A:
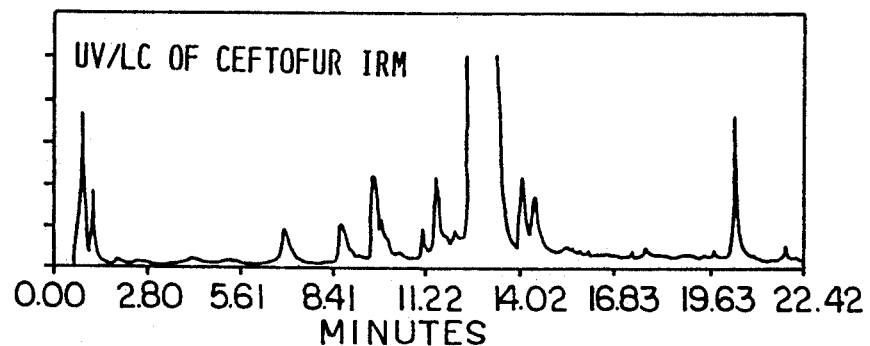
Figure 11B:
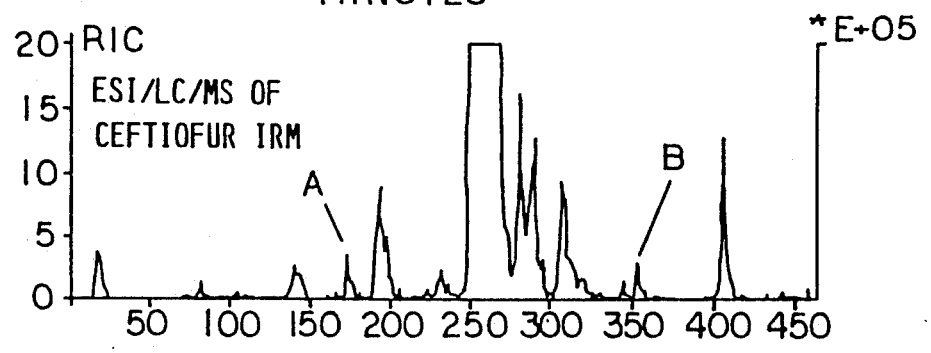
Figure 11C:
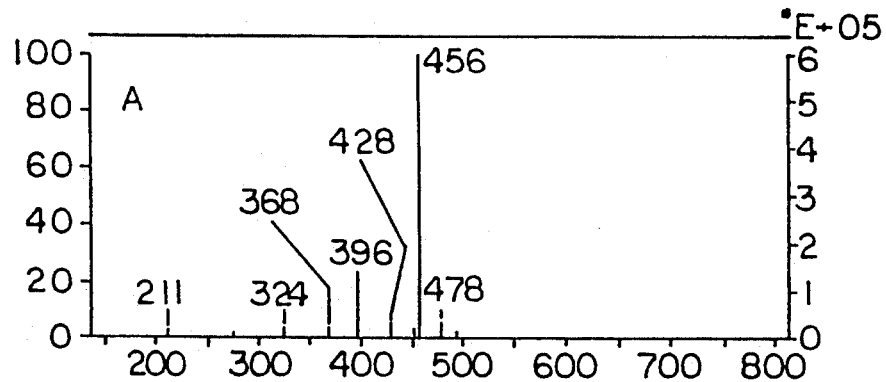
Figure 11D:
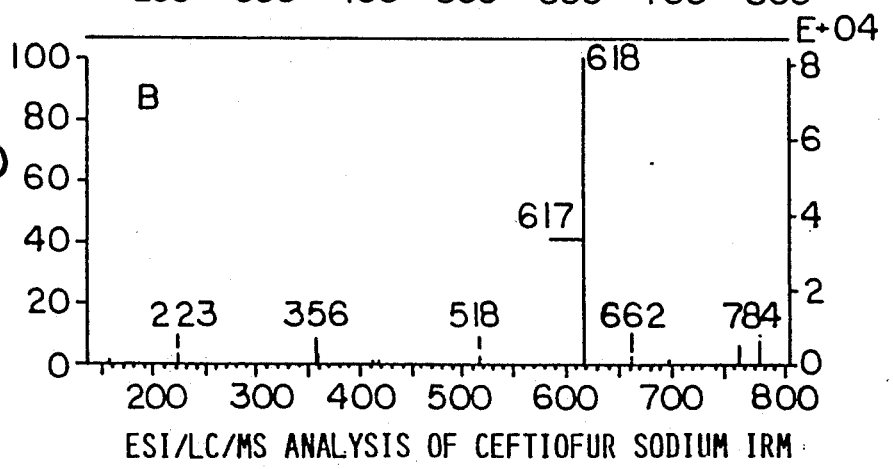

FIG. 9 shows the ESI/MS/MS daughter spectrum of ferterilin acetate (MW=1152). Fifty pmoles of the peptide were infused to the interface via split flow injection without chromatography. The doubly charged parent ion at m/z=577 was preselected by the first analyzer and collisionally activated in the collision quadrupole with argon (0.8 torr) at a lab collision energy of $-25eV$. The resultant daughters ions were analyzer with the third analytical quadrupole in the conventional manner. Although peptide MS/MS fragmentation schemes are beyond the scope of this text, complete sequence information for this peptide is derived from the significant b-series (N-terminal) and y-series (C-terminal) fragment ions. The S/N ratio of this spectrum at the 50 p moles level demonstrates the capabilities of the technique and a marked improvement over TSP/MS/MS methods. Interpretable ESI/MS/MS data could be obtained for ferterilin acetate using less than 500 femtomoles to material exceeding the sensitivity observed using any other primary ionization mode.

Despite the central interest in biopolymer analysis by ESI, the mainstay of pharmaceutical LC/MS remains the analysis of small molecule drug entities and related low level minor components. TSP applications abound in the literature but to date fee small molecule ESI applications have been published. Soft ion evaporation primary ionization provides molecular weight and structural information for extremely labile species not amenable to conventional electron impact and chemical ionization thermal desorbtion methods.

Cephalosporin antibiotics have been particularly challenging owing to their thermal and hydrolytic lability. TSP analysis of cephalosporins has been effective, but requires the use of sub-optimum interface temperatures to prevent solution state hydrolysis of the sample. TSP sensitivity is commensurately poor. FIG. 10 shows the ESI spectrum obtained for 100 pg of ceftiofur sodium infused to the interface by split flow injection. Sensitivity is good with the sodium cationized parent ion clearly observed at m/z=546. No sample hydrolysis is evident from the absence of the lactam hydrolysis product at m/z=243.

Analysis of Ceftiofur Impurities Reference Material (IRM) is shown in FIG. 11. This sample contained the bulk drug and numerous impurities at individual levels ranging from 0.1 to 2.0 weight percent. A 20 mcg sample of the IRM was chromatographed suing a Zorbax RX C8 (4.6 mm×25 cm) column and 0-100% acetonitrile gradient in 30 minutes. Column eluent was conveyed to the interface via the spitter as before. MS RIC data exhibits good S/N and ion current stability and agrees well with the UV chromatogram. Unsubtracted spectra for two of the minor components similarly show good S/N with little or no sample decomposition. MS chromatographic fidelity is excellent with no peak "ghosting". It was not necessary to divert the major component peak to waste to prevent source fouling as with TSP allowing easy detection of minor components on the tailing edge of the major component peak and obviating the need for operator attendance during data acquisition.

A 20 mcg sample of the cardiac antiarrhythmic drug U-70,226E was likewise chromatographed using similar conditions as shown in FIG. 12. Two minor process impurities "A" and "B" near 0.1 weight percent are clearly observed in the MS RIC data on the trailing edge of the major component peak. Again, the major component did not have to be vented to waste allowing detection of these species. Excellent spectra were obtained for these minor components as shown in the figure.

Figure 13A:
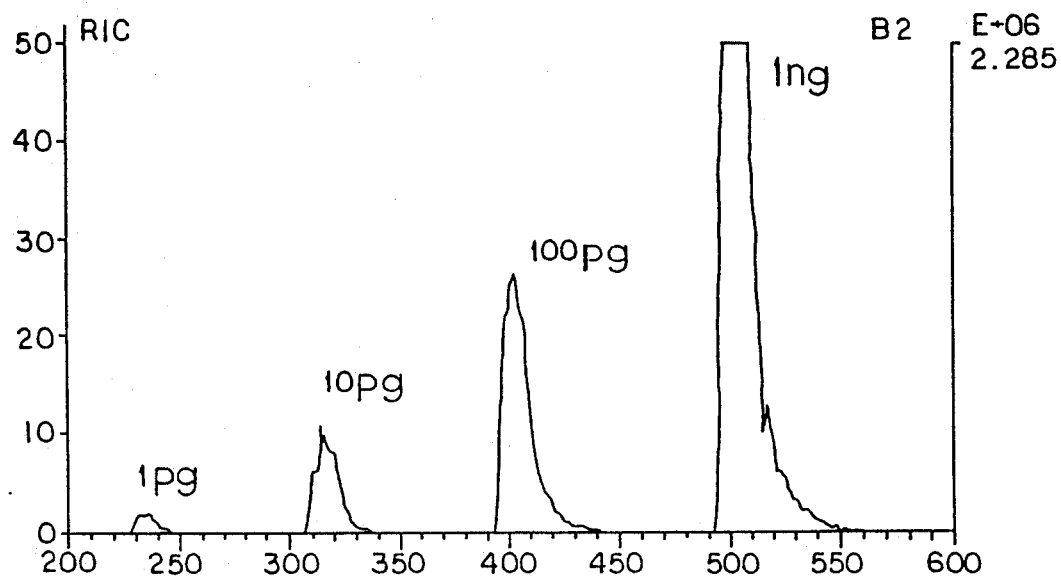
Figure 13B:
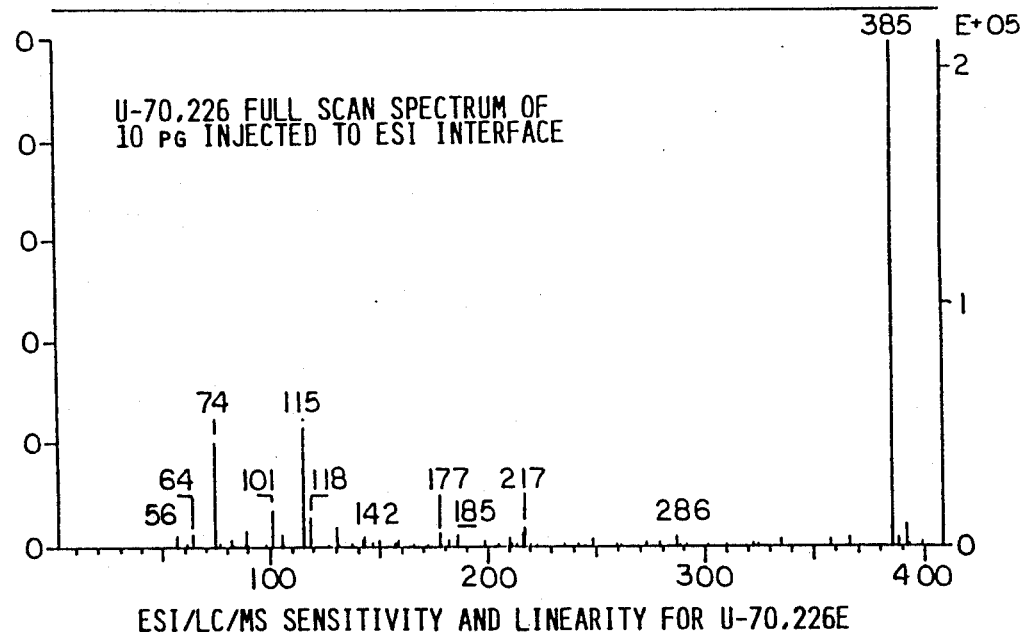
Figure 15A:
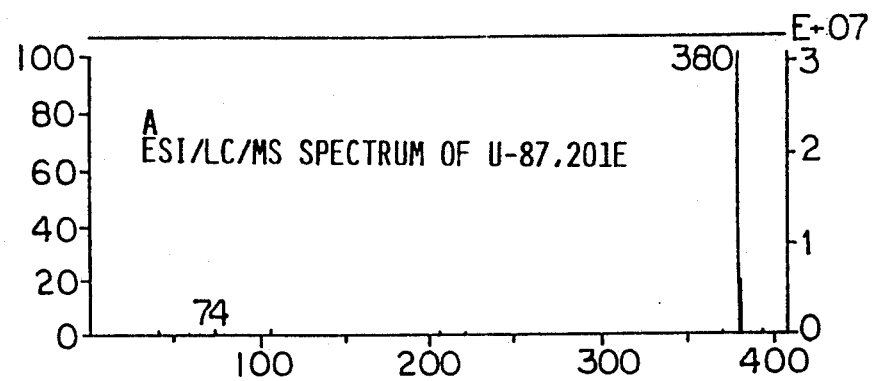
Figure 15B:
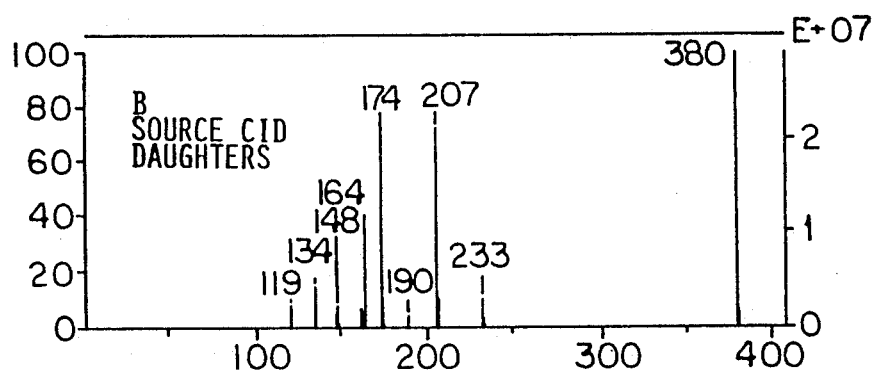
Figure 15C:
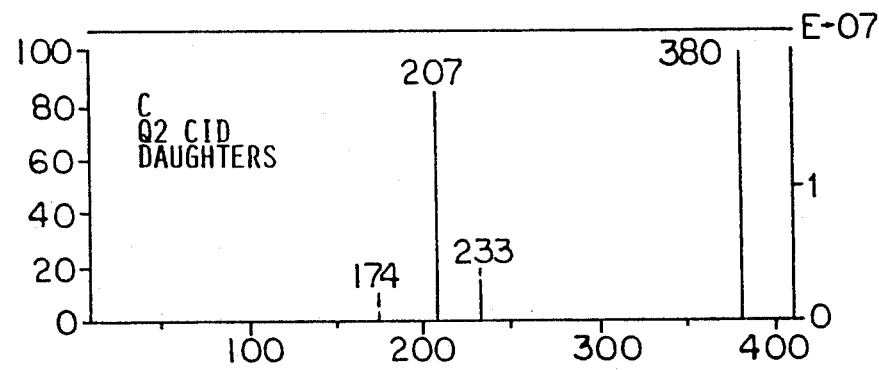
Figure 15D:
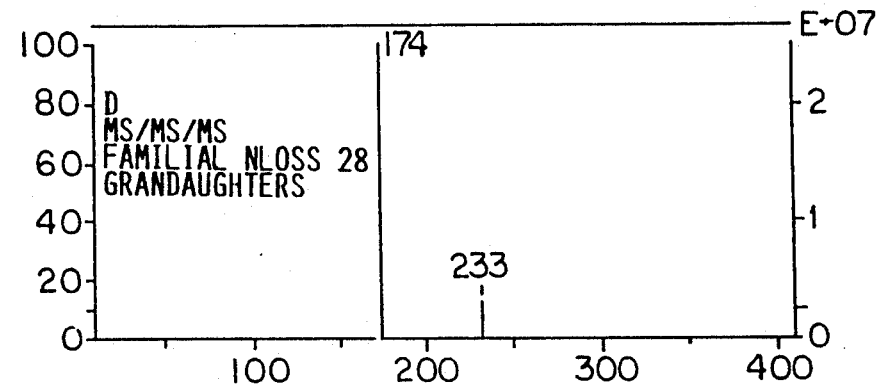

FIG. 13 summarizes an ESI sensitivity test for U-70,226E. Serial dilutions of the drug were introduced by split flow injection without chromatography. Selected Ion current Monitoring (SIM) was employed for the m/z=385 parent ion. This ion current was sampled for 200 msec four times per second. The SIM chromatographic traces show remarkable ion current stability however, the ESI response curve is clearly non-linear as evidence by relative peak areas. ESI appears to have a compressed dynamic range relative to TSP. The 1 pg injection was not significantly above blank but the full scan spectrum for a 10 pg injection exhibits reasonable S/N.

FIG. 14 summarizes a series of MS/MS structural experiments for U-70,226E acquired by repetitive infusion of 500 pg of the bulk drug. Frame A shows the standard ESI/MS spectrum of the drug with protonated molecular ion at m/z=385 and no fragmentation. Frame B shows the ESI source induced CID daughter spectrum acquired by raising the probe bias potential to 100 volts. Collisional activation within the skimmer region yields significant fragmentation as shown. Frame C is the conventional triple quadrupole CID daughter spectrum of the selected m/z=385 parent ion which corresponds well to the source induced CID spectrum.

Source induced CID provides for pseudo MS/MS/MS analysis by initial fragmentation of the single (unselected) parent in the ESI source followed by conventional triple quadrupole parent, daughter or neutral loss scanning. Frame D shows the "granddaughter" spectrum of the m/z=144 primary daughter ion. U-70,226E was fragmented by ESI source induced CID to produce the m/z=144 daughter ion. This ion was preselected for secondary CID in the conventional manner to yield the daughter spectrum shown. Aromatic fragment ions at m/z=91 and 77 are clearly observed confirming this substructure of the 144 ion. Collisional scattering reduces the ion transmission efficiency of the ESI source significantly reducing sensitivity in the source induced CID mode.

Similarly, MS/MS spectra were recorded for Reverse Transcriptase Inhibitor (RTI) as shown in FIG. 15. Frame A shows the RTI protonated parent ion at m/z=380 with no fragmentation. Frame B shows the ESI source induced CID spectrum obtained by raising the probe bias potential to 125 volts. Frame C is the conventional triple quadrupole daughter spectrum of the preselected m/z=380 parent ion. Frame D shows the familial neutral loss 28 granddaughter spectrum. RTI was initially fragmented by source induced CID to yield daughters ions. These daughters were introduced to the triple quadrupole scanning with neutral loss offset of 28 amu. The resulting neural loss granddaughter spectrum contains only those daughter ions which lose 28 amu or C=O. This confirms that the m/z=174 and 233 fragments contain the carbonyl. Pseudo MS/MS/MS analysis finds application in the unambiguous assignment of nominal mass daughter spectra were mass degeneracy hinders interpretation. These techniques are best suited to application were sample is not limited.

These foregoing data illustrate the basic capabilities of the probe based ESI interface and its application to pharmaceutical development problems. The performance of the device meets of exceeds that of commercial designs for similar applications documented in the literature.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In a thermospray equipped LC/MS analyzer having an ion source body member with a first means defining a passageway therethrough, said passageway having an inlet end and an outlet end oriented at spaced locations on said body member, second means defining an inlet orifice in an internal wall of said passageway, said inlet orifice providing ion communication between the passageway and a first chamber containing the analyzer, vacuum source means connected to said outlet end of said passageway and said first chamber, said second means including a skimmer cone encircling said inlet orifice for focusing the ions entering the inlet orifice and the analyzer, third means defining an opening through the wall of the body member and opening into said passageway for providing communication between an area outside of said housing member and said passageway, said opening being generally axially aligned with the inlet orifice, and an electrospray means for spraying charged micron size droplets of a solution of molecules of interest, the improvement wherein:

an elongated probe means is provided and includes an elongated and hollow second chamber opened at one end to atmosphere and closed at the other end by a first partition;
fourth means defining a first hole through said first partition;
a second partition in said second chamber spaced from said first partition and defining a third chamber therebetween;
an elongated and hollow probe shaft connected to and extending from said first partition on a side thereof remote from said open end, a central axis of said probe shaft being coaxial with a central axis of said first hole;
an elongated and hollow drift tube and first heater means for regulating the temperature of said drift tube mounted inside said probe shaft, an inlet end of said drift tube extending through said first hole in said first partition and terminating in said third chamber, an outlet end of said drift tube extending a finite distance beyond an end of said probe shaft remote from said first partition;
adjustment means for selectively adjusting the spacing between said first and second partitions;
fifth means defining a second hole in said second partition coaxially aligned with said first hole, the relative spacing between said first and second partitions determining a spacing between said inlet end of said drift tube and said second hole;
dry gas passageway means for facilitating a supply of dry gas to said third chamber and said second hole;
second heater means for controlling the temperature of said second chamber, and
plug means for closing said inlet end of said passageway in said body member;
whereby the outlet end of said drift tube is connected to said third means, and whereby the spray of charged droplets into said first chamber will be drawn toward said second partition and through said second hole therethrough and thence into said inlet end of said drift tube for subsequent delivery to said passageway in said body member and thence said inlet orifice to said analyzer.

2. A probe adapter for converting a thermospray equipped LC/MS analyzer to an electrospray equipped LC/MS analyzer, comprising:

first means defining an elongated and hollow first chamber opened at one end to atmosphere and closed at the other end by a first partition;
second means defining a first hole through said first partition;
a second partition in said first chamber spaced from said first partition and defining a second chamber therebetween;
an elongated and hollow probe shaft connected to and extending from said first partition on a side thereof remote from open end, a central axis of said probe shaft being coaxial with a central axis of said first hole;
an elongated and hollow drift tube and mounted inside said probe shaft, an inlet end of said drift tube extending through said first hole in said first partition and terminating in said second chamber, an outlet end of said drift tube extending a finite distance beyond an end of said probe shaft remote from said first partition;
adjustment means for selectively adjusting the spacing between said first and second partitions; and
third means defining a second hole in said second partition coaxially aligned with said first hole, the relative spacing between said first and second partitions determining a spacing between said inlet end of said drift tube and said second hole.

3. The probe shaft adapter according to claim 2, wherein an annular space is defined between said elongated and hollow drift tube and the interior surface of said elongated and hollow probe shaft; and wherein heater means is provided in said space; and wherein insulation means is provided between said heater means and said drift tube and said probe shaft.

4. The probe shaft according to claim 3, wherein said drift tube includes a heater support tube oriented concentrically about said drift tube, an annular space being provided therebetween; and wherein spacer members are provided between the exterior of said drift tube and the interior of said heater support tube; and wherein said heater means and said insulation means are provided in the space between said heater tube and the interior surface of said probe shaft.

5. The probe shaft according to claim 2, wherein said second chamber includes means defining a passageway for facilitating the introduction of a drying gas into said second chamber.

6. The probe shaft according to claim 2, wherein heater means are provided for heating the first chamber.

7. The probe shaft according to claim 2, wherein first heater means for heating said probe shaft are provided on said probe shaft; and wherein second heater means for heating said first chamber are provided on said first means; and wherein monitoring means are provided for monitoring and controlling the temperature of said probe shaft and said first means.

8. The probe shaft according to claim 2, wherein said probe shaft is connected to an electrical power supply adapted to apply a voltage thereto in the range of 0 volts to 300 volts.

* * * * *